(12) United States Patent
Inada et al.

(10) Patent No.: US 7,022,989 B2
(45) Date of Patent: *Apr. 4, 2006

(54) METHOD AND DEVICE FOR OBSERVING A SPECIMEN IN A FIELD OF VIEW OF AN ELECTRON MICROSCOPE

(75) Inventors: Hiromi Inada, Hitachinaka (JP); Isao Nagaoki, Hitachinaka (JP); Hiroyuki Kobayashi, Mito (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/800,872

(22) Filed: Mar. 16, 2004

(65) Prior Publication Data

US 2004/0173749 A1 Sep. 9, 2004

Related U.S. Application Data

(63) Continuation of application No. 09/871,739, filed on Jun. 4, 2001, now Pat. No. 6,878,934.

(30) Foreign Application Priority Data

Jul. 13, 2000 (JP) .............................. 2000-212961

(51) Int. Cl.
*G01N 23/00* (2006.01)
(52) U.S. Cl. ..................................... 250/311
(58) Field of Classification Search ................ 250/307, 250/311, 400
See application file for complete search history.

(56) References Cited

U.S. PATENT DOCUMENTS

| 3,700,801 A | 10/1972 | Dougherty |
| 5,084,618 A | 1/1992 | Ito |
| 5,134,288 A | 7/1992 | Van Dijck |
| 5,350,921 A | 9/1994 | Aoyama et al. |
| 5,466,934 A | 11/1995 | Adams et al. |

FOREIGN PATENT DOCUMENTS

| JP | 06-215720 | 5/1994 |
| JP | A-8-298090 | 11/1996 |
| JP | 10-172488 | 6/1998 |

OTHER PUBLICATIONS

Kobayashi, K., "Principles of Phase Only Correlation and Its Applications", ITE Technical Report vol. 20, No. 41, pp. 1-6, MIP 96-53, NIM 96-75 (Jul. 1996).

*Primary Examiner*—Thinh Nguyen
(74) *Attorney, Agent, or Firm*—Dickstein Shapiro Morin & Oshinsky LLP

(57) ABSTRACT

The present invention provides a method of observing a specimen in a field of view of an electron microscope comprising the acts of illuminating the specimen with an electron beam having a first angle and forming a first transmission image of the specimen in the field of view and adjusting the electron beam to a second angle and forming a second transmission image of the specimen in the field of view and calculating a degree of coincidence between the first and second transmission images.

3 Claims, 16 Drawing Sheets

EXAMPLE OF MAGNIFIED
SAMPLE TRANSMISSION IMAGE

EXAMPLE OF MAGNIFIED
SAMPLE TRANSMISSION
IMAGE (LOW CONTRAST)

FIG. 5A
FIG. 5B
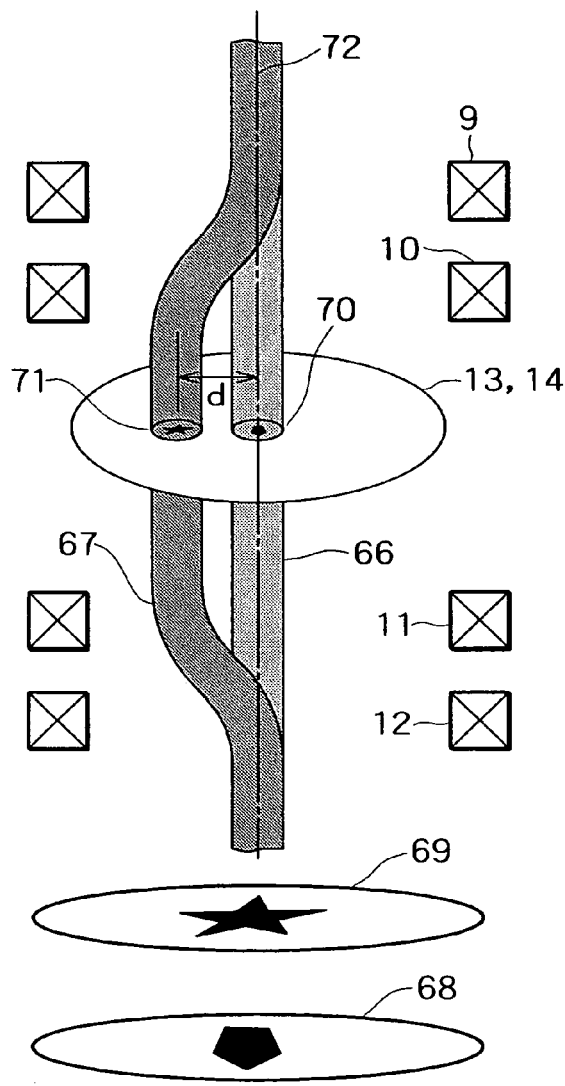
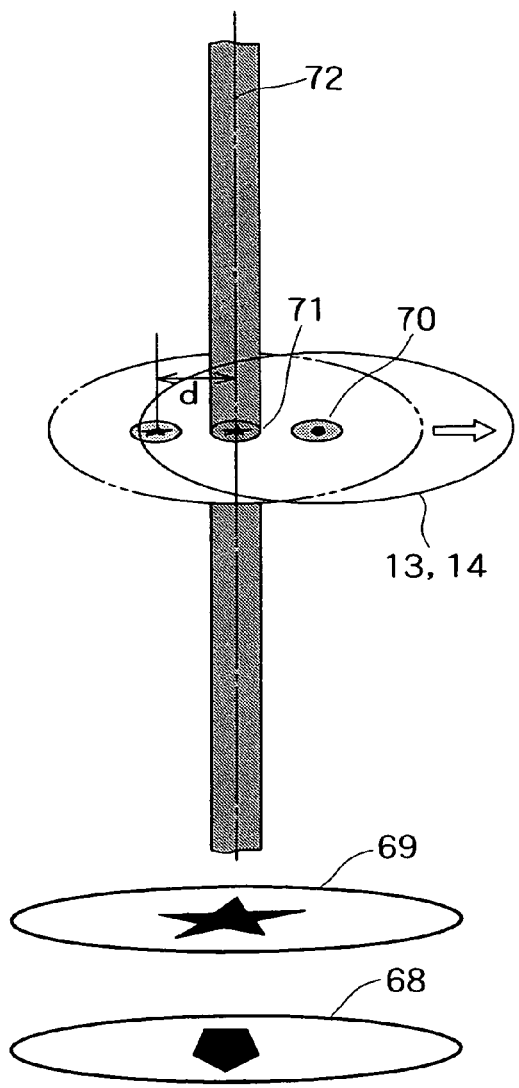
ELECTROMAGNETIC MOVEMENT OF FIELD OF VIEW USING ELECTRON BEAM DEFLECTING COIL
MECHANICAL MOVEMENT OF FIELD OF VIEW USING SAMPLE STAGE DRIVER FIG. 13 (1)
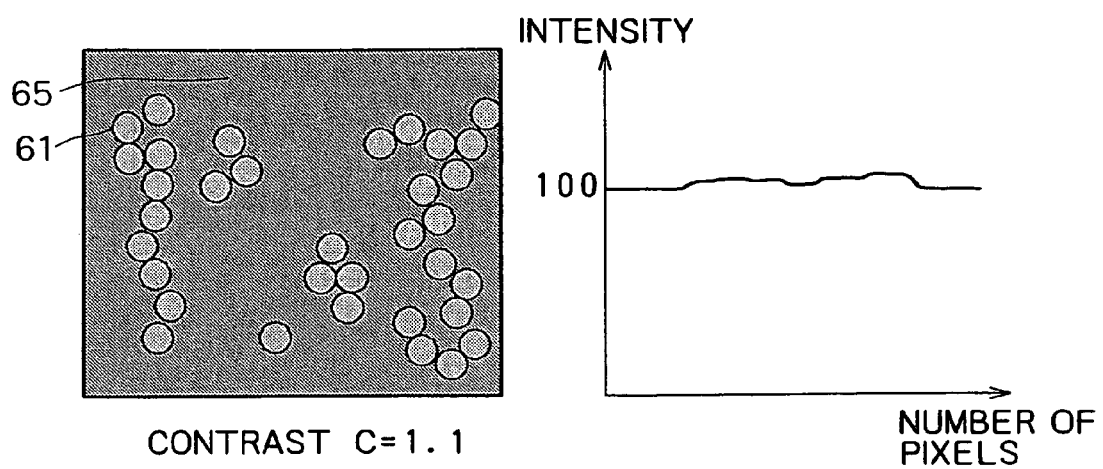
CONTRAST C=1.1
FIG. 13 (2)
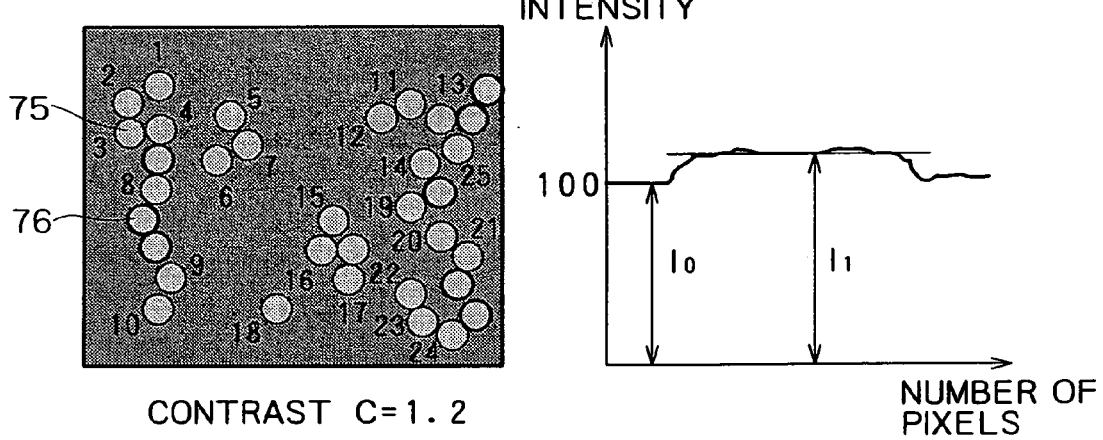
CONTRAST C=1.2
FIG. 13 (3)
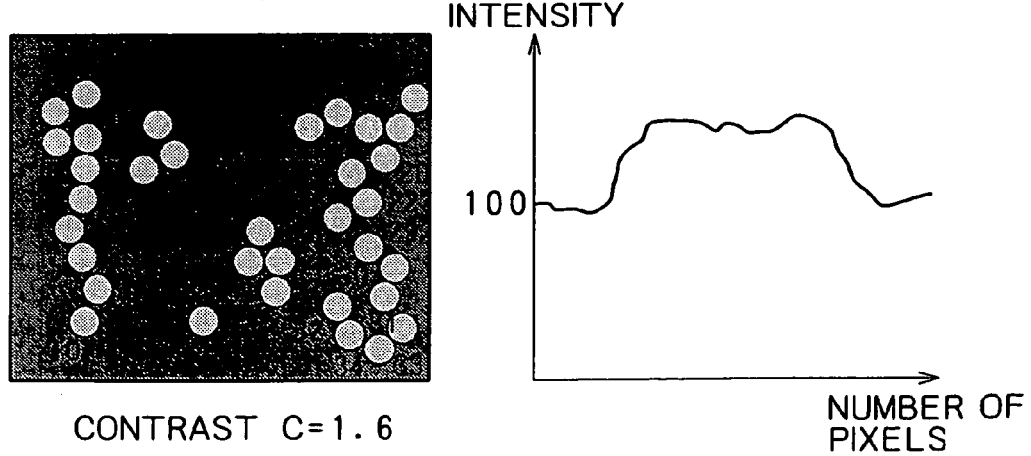
CONTRAST C=1.6 ns US 7,022,989 B2

METHOD AND DEVICE FOR OBSERVING A SPECIMEN IN A FIELD OF VIEW OF AN ELECTRON MICROSCOPE

CROSS REFERENCE TO RELATED APPLICATIONS

The present application is a continuation application of U.S. patent application Ser. No. 09/871,739, filed on Jun. 4, 2001 now U.S. Pat. No. 6,878,934, the disclosure of which is herewith incorporated by reference in its entirety.

FIELD OF THE INVENTION

The present invention relates generally to electron microscopes, and particularly, to a method and device for observing a specimen in a field of view of an electron microscope.

DISCUSSION OF THE RELATED ART

When a specimen (sample) transmission image in a field of view is measured, analyzed or searched by a conventional electron microscope, the operator directly operates the specimen stage and corrects focus thereby locating a desired field of view in a magnified specimen transmission image projected on a scintillator. This operation is very complex, time-consuming and tedious for the operator. As a result, this operation invites human error such as overlooking a necessary field of view and reducing observation efficiency and accuracy.

For instance, as shown in FIG. 2, when a specimen image is to be observed or a field of view is to be searched, a thin-film specimen to be observed is mounted on a specimen holding mesh or a micro-grid and the specimen holding mesh or the micro-grid is fixed to a specimen holder. When a region to be searched is divided into nine sections, as shown in FIG. 2, magnified transmission images of the specimen are classified into three types as shown in FIGS. 2(A), 2(B), and 2(C). When observing a field of view, such as field "5" (FIG. 2(B)), a magnified transmission image of a form 61 on the specimen can be obtained. But, when the observing field of view is "1," "4," or "7" in FIG. 2, a magnified transmission image of only a shadow or an edge portion of the specimen holding mesh is obtained and therefore the entire field of view is completely dark (FIG. 2(A)). Also, when the observing field of view is, for instance, field "9," nothing is present in the field of view and therefore it is completely white (FIG. 2(C)). These fields of view, namely, "1," "4," "7" and "9," are not appropriate for observation.

Thus, with conventional methods and devices for observing a specimen in a field of view of an electron microscope, it is not possible to efficiently exclude fields of view inappropriate for observation, search, or analysis as shown in FIGS. 2(A) and 2(C). In other words, when the conventional electron microscope automatically moves a field of view to search for a target form, the conventional electron microscope searches both a field of view appropriate for search in which the specimen is present and an unnecessary field of view inappropriate for search in which the specimen is not present.

SUMMARY OF THE INVENTION

It is accordingly an object of the present invention to provide a method and device for observing a specimen in a field of view of an electron microscope that can automatically and efficiently determine whether or not a picked-up field of view is appropriate for making a search for a target form of a specimen and thereby efficiently extract only necessary fields of view.

In an object of the present invention, a method of observing a specimen in a field of view of an electron microscope is provided, comprising the acts of setting the magnification of the electron microscope, setting conditions for moving the field of view, setting a starting position for the field of view and moving the field of view based upon the condition. Further, the invention provides illuminating the specimen with an electron beam having a first angle and forming a first transmission image of the specimen in the field of view, adjusting the electron beam to a second angle and forming a second transmission image of the specimen in the field of view and calculating a degree of coincidence between the first and second transmission images.

In another object of the present invention, a method of observing a specimen in a field of view of an electron microscope is provided, comprising the acts of setting the magnification of the electron microscope, setting conditions for moving the field of view, setting a starting position for the field of view and moving the field of view based upon the condition. The invention further provides illuminating the specimen with an electron beam in one direction and forming a line profile transmission image of the specimen in the field of view and then observing the field of view if a change in the line profile is found.

In yet another object of the present invention, a method of observing a specimen in a field of view of an electron microscope is provided comprising the acts of setting the magnification of the electron microscope, setting conditions for moving the field of view, setting a starting position for the field of view and moving the field of view based upon the condition. The invention further provides illuminating the specimen with an electron beam and forming a transmission image of the specimen in the field of view, selecting a pattern from the transmission image and matching the selected pattern with a preset pattern and observing the field of view if a match is found between the selected pattern and the preset pattern.

In an object of the present invention, an electron microscope is provided comprising a support for supporting a specimen, a deflector for deflecting an electron beam to the specimen to create a transmission image, an image pickup device for obtaining the transmission image and a processor coupled to the image pickup device being programmed for observing a specimen in a field of view of an electron microscope. The programming comprises the acts of setting the magnification of the electron microscope, setting conditions for moving the field of view, setting a starting position for the field of view and moving the field of view based upon the condition, The invention further provides illuminating the specimen with an electron beam having a first angle and forming a first transmission image of the specimen in the field of view, adjusting the electron beam to a second angle and forming a second transmission image of the specimen in the field of view and calculating a degree of coincidence between the first and second transmission images.

In another object of the present invention an electron microscope is provided comprising a support for supporting a specimen, a deflector for deflecting an electron beam to the specimen to create a transmission image, an image pickup device for obtaining the transmission image and a processor coupled to the image pickup device being programmed for observing a specimen in a field of view of an electron microscope. The programming comprises the acts of setting the magnification of the electron microscope, setting conditions for moving the field of view, setting a starting position for the field of view and moving the field of view based upon the condition. The invention further provides illuminating the specimen with an electron beam in one direction and forming a line profile transmission image of the specimen in the field of view and observing the field of view if a change in the line profile is found.

In yet another object of the present invention an electron microscope is provided comprising a support for supporting a specimen, a deflector for deflecting an electron beam to the specimen to create a transmission image, an image pickup device for obtaining the transmission image and a processor coupled to the image pickup device being programmed for observing a specimen in a field of view of an electron microscope. The programming comprises the acts of setting the magnification of the electron microscope, setting conditions for moving the field of view, setting a starting position for the field of view and moving the field of view based upon the condition. The invention further provides illuminating the specimen with an electron beam and forming a transmission image of the specimen in the field of view selecting a pattern from the transmission image and matching the selected pattern with a preset pattern and observing the field of view if a match is found between the selected pattern and the preset pattern.

BRIEF DESCRIPTION OF THE DRAWINGS

The above advantages and features of the invention will be more clearly understood from the following detailed description which is provided in connection with the accompanying drawings.

FIGS. 5(a) and 5(b) illustrates a method of moving a field of view;

FIGS. 13(1), 13(2), and 13(3) illustrates contrasts and signal intensity distributions of a specimen transmission image;

DETAILED DESCRIPTION OF THE INVENTION

Figure 1:
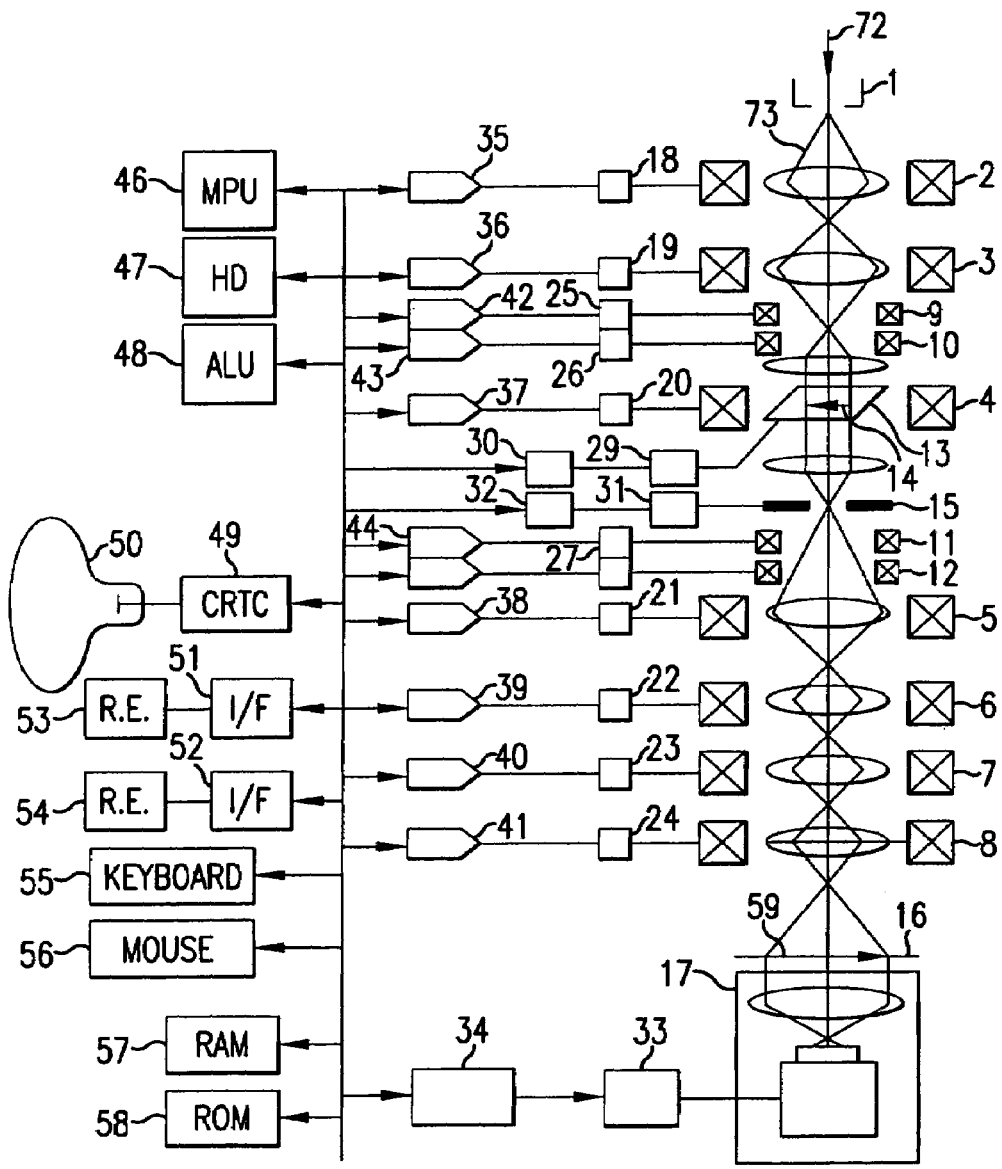
FIG. 1 is a block diagram illustrating an example of an electron microscope according to the present invention.

Exemplary embodiment of the present invention will be described below in connection with the drawings. Other embodiments may be utilized and structural or logical changes may be made without departing from the spirit or scope of the present invention. Like items are referred to by like reference numerals throughout the drawings.

Referring now to the drawings, FIG. 1 illustrates a schematic functional block diagram showing an example of a transmission electron microscope according to the present invention. Although any number of electron beam deflecting coils may be employed, two deflecting coils over a specimen and two deflecting coils under the specimen or a total of four electron beam deflecting coils are used as an example in this case. It is to be noted that all of the embodiments below will be described on an assumption that they employ the transmission electron microscope shown in FIG. 1.

An electron beam 73 emitted from an electron gun 1 and then accelerated is applied through magnetic fields of a first irradiation lens coil 2, a second irradiation lens coil 3, and an objective lens coil 4 to a specimen 14 held on a specimen stage 13. The electron beam 73 transmitted by the specimen 14 is magnified by a first intermediate lens coil 5 and a second intermediate lens coil 6, and then further magnified by a first projection lens coil 7 and a second projection lens coil 8, whereby a magnified transmission image 59 of the specimen is formed on a scintillator 16. In this example, coils using electromagnetic field force are used as lenses for deflecting the electron beam and magnifying the specimen transmission image; however, electrostatic deflection and electrostatic lenses using electrostatic force may also be employed to deflect the electron beam and magnify the specimen transmission image.

The magnified transmission image 59 of the specimen converted into an optical image by the scintillator 16 is picked up by a pickup device, for example a TV camera 17. An image signal from the TV camera is captured for processing by a microprocessor 46 via a TV camera controller 33 and an image capturing interface 34, and thereafter displayed as an image on a CRT 50 controlled by a CRT controller 49. In this example, when the magnified transmission image is captured by the microprocessor 46, the scintillator 16 and the TV camera are used; however, a detector such as a MCP (Micro Channel Plate) capable of directly converting an electron beam into an electric signal may also be used.

The microprocessor 46 controls exciting power supplies 18, 19, 20, 21, 22, 23, and 24 that feed the first irradiation lens coil 2, the second irradiation lens coil 3, the objective lens coil 4, the first intermediate lens coil 5, the second intermediate lens coil 6, the first projection lens coil 7, and the second projection lens coil 8 of the transmission electron microscope via DACs (digital-to-analog converters) 35, 36, 37, 38, 39, 40, and 41, respectively. Similarly, the microprocessor 46 controls exciting power supplies 25, 26, 27, and 28 feeding a first deflecting coil 9 and a second deflecting coil 10 over the specimen and a first deflecting coil 11 and a second deflecting coil 12 under the specimen via DACs 42, 43, 44, and 45, respectively.

The microprocessor 46 is connected, via a bus, with an external storage unit 47 such as a hard disk, an arithmetic unit 48, a magnification changing rotary encoder 53, a keyboard 55, a RAM 57, a ROM 58 and the like. The magnification changing rotary encoder 53 is connected to the bus via an I/F (interface) 51. A specimen stage 13 is driven by a fine adjustment motor 29 for driving the stage connected to the microprocessor 46 via a motor driver 30.

Next, as an example of image computation according to the present invention, principles of determining a degree of coincidence between two images by a phase only correlation method and principles of automatic focus correction will be described.

Figure 3A:
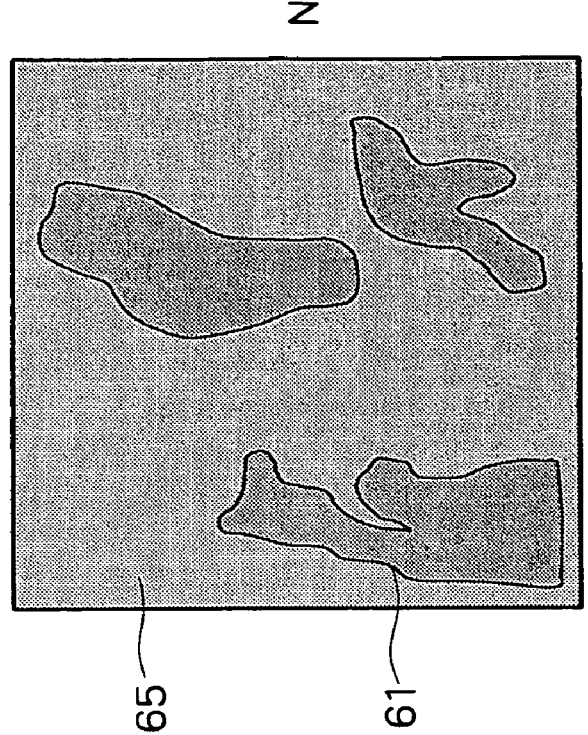
FIGS. 3(A) and 3(B) are diagrams illustrating a specimen transmission image, highlighting the contrast between the background and the specimen form.
Figure 3B:
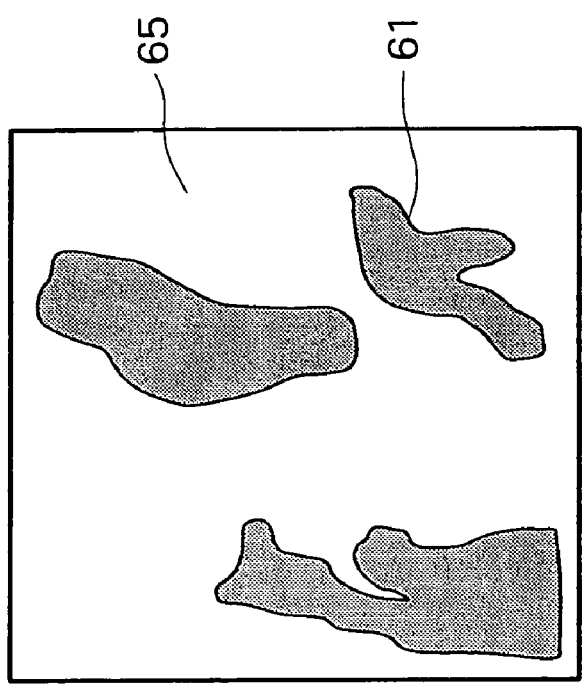

A magnified specimen transmission image 1 of M×N pixels to serve as a reference as shown in FIG. 3(A) is recorded as f1(m, n) in a storage unit. Next, a magnified specimen transmission image picked up by passing a current through two upper electron beam deflecting coils and providing an appropriate inclining deflection angle α to an electron beam applied to the specimen is recorded as a transmission image 2 or f2(m, n) of M×N pixels in the storage unit, where m=0, 1, 2, . . . , M−1; n=0, 1, 2, . . . , N−1.

Discrete Fourier images F1(u, v) and F2(u, v) of the transmission images f1(m, n) and f2(m, n) are defined by the following [Equation 1] and [Equation 2], respectively:

$$F1(u, v) = \sum_{m=0}^{M-1} \sum_{n=0}^{N-1} f1(m, n) e^{-j2\pi(mu/M + nv/N)}$$ [Equation 1]
$$= A(u, v) e^{j\alpha(u,v)}$$

$$F2(u, v) = \sum_{m=0}^{M-1} \sum_{n=0}^{N-1} f2(m, n) e^{-j2\pi(mu/M + nv/N)}$$ [Equation 2]
$$= B(u, v) e^{j\beta(u,v)}$$

where u=0, 1, 2, . . . , M−1; v=0, 1, 2, . . . , N−1; A(u, v) and B(u, v) are amplitude spectra; and α(u, v) and β(u, v) are phase spectra.

According to the phase only correlation method, when an image translation between two images occurs, the position of a correlation peak is displaced by the amount of the translation. A method of deriving an amount of translation will be described in the following. First, it is assumed that when the transmission image f2(m, n) is translated in a direction of m by r', f3(m, n)=f2(m+r', n). A discrete Fourier image F3(u, v) of f3(m, n) is obtained from [Equation 2 and thereby expressed as [Equation 3].

$$F3(u, v) = \sum_{m=0}^{M-1} \sum_{n=0}^{N-1} f2(m + r', n) e^{-j2\pi(mu/M + nv/N)}$$ [Equation 3]
$$= B(u, v) e^{j(\beta + 2\pi r' u/M)}$$

If the amplitude spectrum B(u, v) is set to be a constant, a phase image not dependent on image contrast and lightness is obtained. A phase image F3'(u, v) of f3 is expressed as the following [Equation 4]. Similarly, a phase image F1'(u, v) of f1 is expressed as the following [Equation 5].

$$F3'(u, v) = e^{j(\beta + 2\pi r' u/M)}$$ [Equation 4]

$$F1'(u, v) = e^{j\alpha(u,v)}$$ [Equation 5]

By multiplying the phase image F1'(u, v) by a complex conjugate of F3'(u, v), a synthetic phase image H13(u, v) represented by the following [Equation 6] is obtained. A correlation strength image or a correlation index (degree of coincidence between two images) g13(r, s) is expressed as the following [Equation 7] as a result of inverse Fourier transformation of the synthetic image H13(u, v).

$$H13(u, v) = F1'(u, v)(F3'(u, v))^*$$ [Equation 6]
$$= e^{j(\alpha - \beta - 2\pi r' u/M)}$$

$$g13(r, s) = \sum_{u=0}^{M-1} \sum_{v=0}^{N-1} (H13(u, v)) e^{j2\pi(ur/M + vs/N)}$$ [Equation 7]
$$= \sum_{u=0}^{M-1} \sum_{v=0}^{N-1} \left( e^{j(\alpha - \beta - 2\pi r' u/M)} \right) e^{j2\pi(ur/M + vs/N)}$$
$$= g12(r - r')$$

When the correlation strength image obtained by [Equation 7] is normalized and a value obtained from [Equation 7] is zero, two images are recognized to be completely different from each other. On the other hand, a value obtained is 100, the two images are recognized to be identical with each other. In other words, a value of "0" is equal to 0% and a value of "100" is equal to 100%.

According to [Equation 7], when there is a positional displacement r' in a direction of m between two images, the correlation peak position of the correlation strength image is displaced by −r'. Thus, the phase only correlation method makes it possible to determine a degree of coincidence and a displacement between a transmission image 1 and a transmission image 2 without depending on the contrast or lightness of the images.

When a peak of a correlation strength image occurs at a position displaced by ΔG [pixel] as a result of computational processing of two specimen transmission images from [Equation 1] to [Equation 7], ΔG [pixel] corresponds to a displacement on a light receiving plane of a detector such as a TV camera, and therefore ΔG is converted into a displacement Δx on the plane of the specimen. The displacement Δx between two images on the plane of the specimen is calculated by the following [Equation 8], where diameter of the detecting light receiving plane is L [m], magnification of the electron microscope on the light receiving plane is M, and the number of pixels of the detector is $L_d$ [pixel]. It is to be noted that [Equation 8] includes an image displacement δ resulting from spherical aberration of an electron lens; therefore a true displacement $\Delta x_t$ of a field of view is obtained by subtracting δ from Δx. The displacement δ on the plane of the specimen is expressed as [Equation 9] by using a spherical aberration Cs and an electron beam deflection angle α. Accordingly, the image displacement $\Delta x_t$ occurring between the two magnified specimen transmission images is represented by [Equation 10].

$$\Delta x = \left( \frac{\Delta G}{L_d} \right) \times \left( \frac{L}{M} \right)$$ [Equation 8]

$$\delta = Cs \cdot \alpha^3$$ [Equation 9]

$$\Delta x_t = \Delta x - \delta \quad \text{[Equation 10]}$$

$$= \left(\frac{\Delta G}{L_d}\right) \times \left(\frac{L}{M}\right) - Cs \cdot \alpha^3$$

A relation between the image displacement $\Delta x_t$ and a focal shift $\Delta f$ is represented by the following [Equation 11]. This relation allows the focal shift $\Delta f$ to be calculated from the image displacement $\Delta x_t$.

$$\Delta f = \frac{\Delta x_t}{\alpha} \quad \text{[Equation 11]}$$

An objective current correction value is calculated from the focal shift $\Delta f$ obtained by [Equation 11]. There is a relation of [Equation 12] between focal length f of the electron lens and an objective lens current I, where N is a number of turns of the electron lens coil, E* is an accelerating voltage obtained by relativistic correction, and I is an objective lens current value. Thus, focusing is attained by adding the objective current correction value obtained from the relation of [Equation 12] to the objective current value.

$$f \propto \left(\frac{IN}{\sqrt{E^*}}\right)^2 \quad \text{[Equation 12]}$$

Embodiments of the present invention will next be specifically described.

Figure 4:
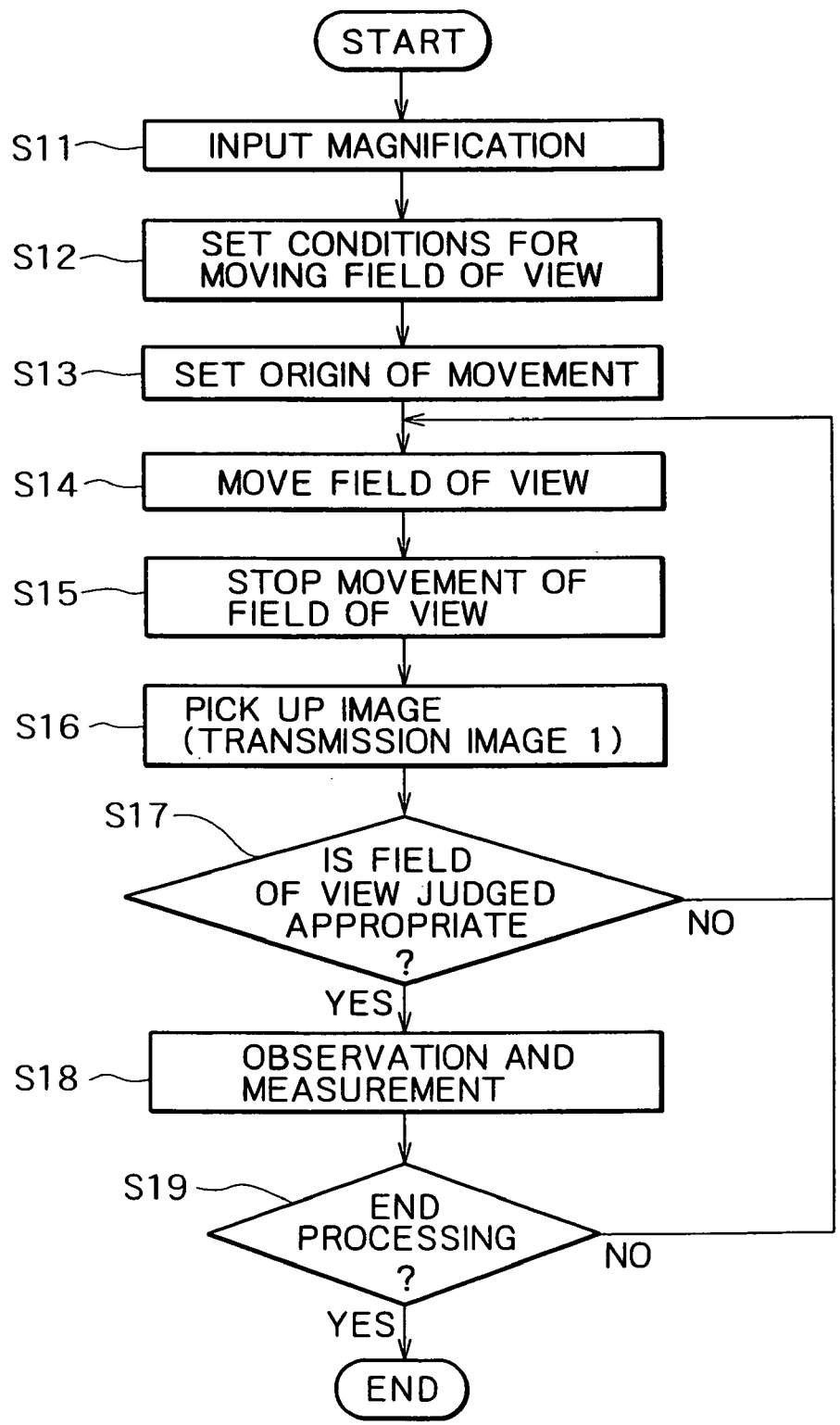
FIG. 4 is a flowchart illustrating a method which comprises automatically moving or selecting a field of view and determining whether the field of view has a brightness appropriate for observation or search.

FIG. 4 is a flowchart of a first embodiment showing a method comprising the steps of automatically moving or selecting a field of view, determining whether the field of view has a brightness (gradation) inappropriate for observation or search, and then efficiently observing or searching for only an appropriate field of view by using the transmission electron microscope shown in FIG. 1.

At a step 11 in FIG. 4, magnification of the transmission electron microscope is set so as to obtain an arbitrary specimen transmission image. The magnification for the specimen transmission image is inputted by the magnification changing rotary encoder 53. A pulse wave generated by the rotary encoder 53 is converted into a digital signal by the I/F 51. On the basis of the digital signal inputted from the I/F 51, the microprocessor 46 refers to magnification display data preset in the ROM 58 to display a corresponding magnification on the CRT 50. At the same time, the microprocessor 46 outputs data of the first irradiation lens coil 2, the second irradiation lens coil 3, the objective lens coil 4, the first intermediate lens coil 5, the second intermediate lens coil 6, the first projection lens coil 7, and the second projection lens coil 8, which data is prestored in the ROM 58, to the DACs 35, 36, 37, 38, 39, 40, and 41, respectively, so that data of the lens system is converted into analog signals. The DACs output analog signals to the exciting power supplies 18, 19, 20, 21, 22, 23, and 24 to pass current through the lens coils of the lens system.

Next, conditions for automatically moving a field of view are set at a step 12. A moving speed of the field of view and a range of search are inputted by the keyboard 55 or a mouse 56, then processed by the microprocessor, and stored in the storage unit.

At a step 13, an origin of field movement is set. As shown for example in FIG. 2, the origin 64 of field movement is set at a corner of a field of view displayed on the display apparatus (CRT) 50 by using an input device such as a mouse. A coordinate position set as the origin by the processing of the microprocessor 46 is stored in the storage unit 47.

Figure 2:
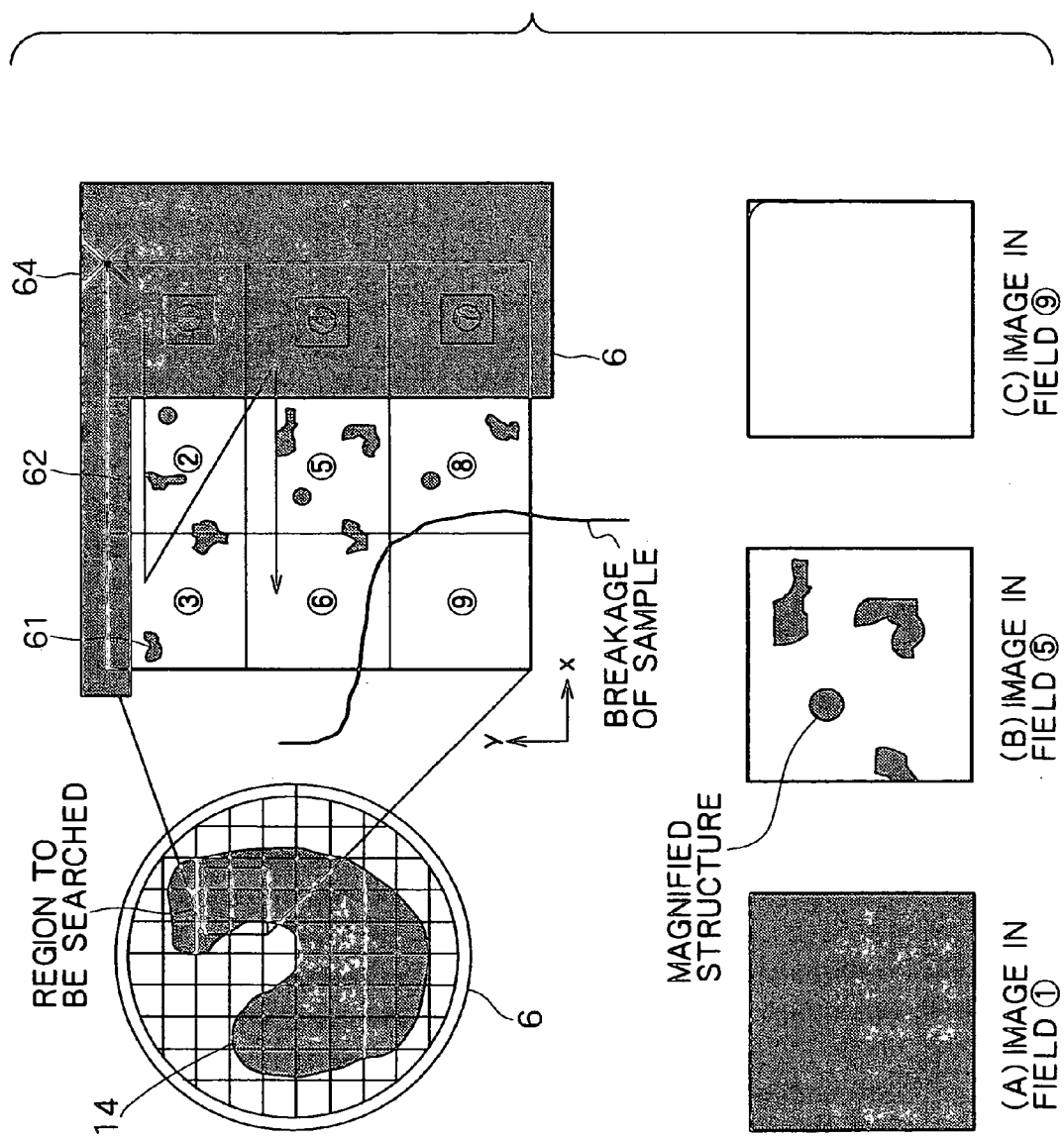
FIG. 2 is a schematic diagram illustrating specimen observation or search by automatically moving a field of view.

At a step 14, the field of view is moved in a sequence of "1"→"2"→"3"→ . . . "9" in FIG. 2, for example, under the conditions for moving the field of view set at the steps 12 and 13. It is to be noted that the movement of the observing field of view 62 is not limited to the sequence from the field "1" to the field "9," as shown in FIG. 2, rather, the observing field of view 62 may be moved to a randomly selected field. The observing field of view may be moved by an electromagnetic method using electron beam deflecting coils disposed over and under the specimen, a mechanical method using a specimen stage driver, or a stage driving mechanism using a piezoelectric device or the like.

FIG. 5(a) is a schematic diagram of assistance in explaining a method of electromagnetically moving the field of view. At a command from the microprocessor 46, and under the conditions for moving the field of view set at the step 12, the two electron beam deflecting coils disposed over the specimen (the first deflecting coil 9 and the second deflecting coil 10 over the specimen) translate the electron beam 73 from a position of an electron beam optical axis 72 passing through a field 70 at the center of the specimen to that of a deflected electron beam 67. The electron beam 73 is thus applied to the specimen 14. The deflected electron beam 67 is applied to a field 71 at a distance d from the center of the specimen. The electron beam after passing through the specimen is returned to the electron beam optical axis 72 by the electron beam deflecting coils disposed under the specimen, that is, the first deflecting coil 11 and the second deflecting coil 12 under the specimen. As a result, a magnified specimen transmission image after the movement of the field of view is obtained.

FIG. 5(b) is a schematic diagram of assistance in explaining a method of mechanically moving the field of view. In this case, the microprocessor 46 controls the motor driver 30 under the conditions for moving the field of view set at the step 12 and thereby drives the fine adjustment mechanism 13 for the specimen stage by means of the stage driving motor 29 to slightly move the specimen. In the case of the field moving method using a piezoelectric device, the stage driving motor is replaced with a piezoelectric device to perform slight movement of the specimen.

At a step 15 in FIG. 4, the movement of the field of view is stopped. Conditions for stopping the movement of the field of view are determined by the conditions for moving the field of view set at the step 12 and a size of each field of view defined by the magnification inputted at the step 11. The field of view is moved and stopped such that an image of the field of view will not be superimposed on an image of the next observing field of view.

At a step 16, a specimen transmission image is picked up in a state in which the field of view is stopped. The electron beam transmitted by the specimen 14 goes through the objective lens 4, the first intermediate lens 5, the second intermediate lens 6, the first projection lens 7, and the second projection lens 8, and then forms a magnified specimen transmission image 59 on the scintillator 16. The TV camera 17 picks up the image projected on the scintillator 16, and the image capturing interface 34 registers the magnified image in the storage unit as a transmission image 1.

At a step 17, whether the transmission image 1 picked up at the step 16 is appropriate for observation or not is determined. Whether the field of view of the transmission image 1 has a brightness (gradation) appropriate for observation or not may be determined by a method of making a line profile of the picked-up field of view and thereby measuring the brightness (gradation), a method of determining a phase-amplitude correlation between two transmission images in the same field of view that are taken under different electro-optical conditions and thereby making a determination by a degree of coincidence between the two images (correlation function), and a method of determining a phase only correlation between two transmission images taken under different conditions and thereby making a determination by a degree of coincidence between the two images. When it is determined that the field of view is not appropriate for observation as a result of determining whether the field of view is appropriate for observation or not by the above determination methods, the processing returns to the step 14. On the other hand, when it is determined that the field of view is appropriate for observation, the processing proceeds to a step 18.

Figure 6A:
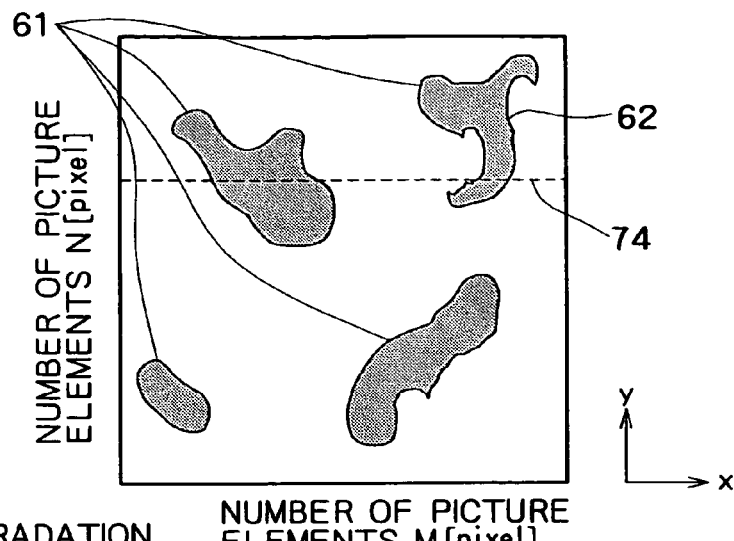
FIGS. 6(A), 6(B), 6(C), and 6(D) are diagrams of line profiles of a specimen transmission image in different field states.
Figure 6B:
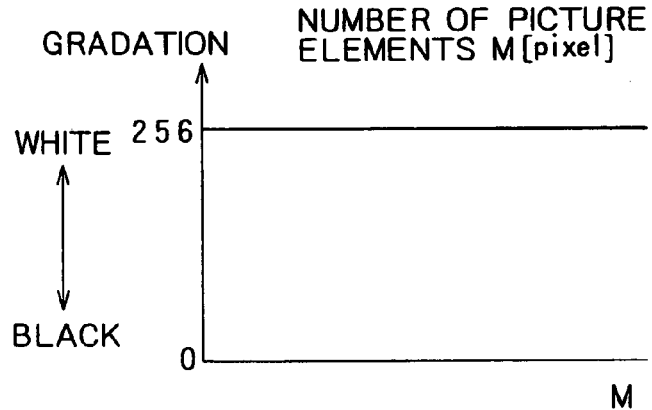
Figure 6C:
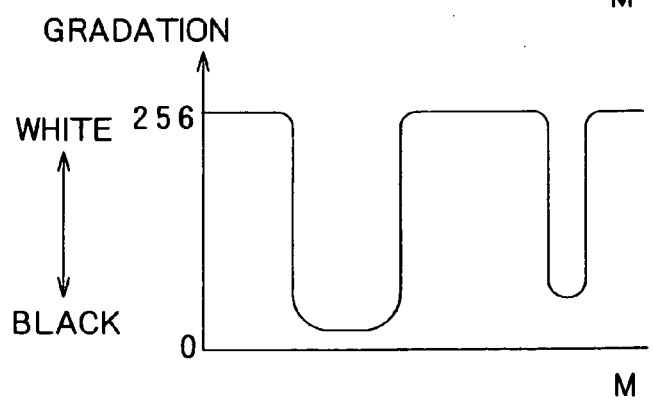
Figure 6D:
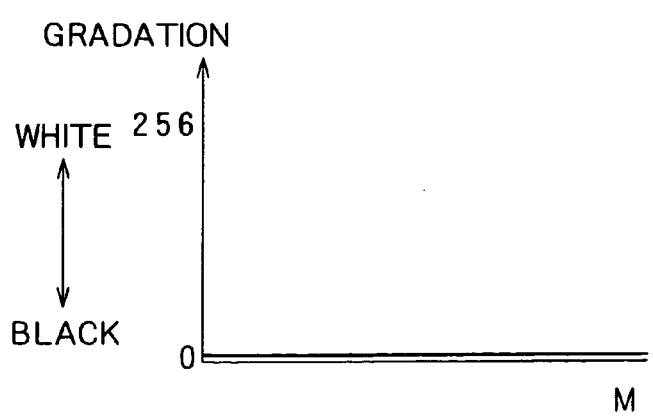

FIGS. 6(A), 6(B), 6(C), and 6(D) are diagrams of assistance in explaining a method of determining a state of a picked-up field of view by using a line profile of the field of view. As shown in FIG. 6(A), x and y coordinates are set and a measuring line 74 as shown in the figure is drawn in an x-direction and/or a y-direction, so that change in brightness on the measuring line is measured as a line profile. FIGS. 6(B), 6(C), and 6(D) each show an example of a result of measurement in the x-direction. In the case of a 256-level gray-scale image, when all the pixels of a line profile have a level 256 or a level zero as shown in FIGS. 6(B) and 6(D) as a result of the measurement, it means that a magnified image of a mesh or a region with no specimen, respectively, is picked up in the field of view, and therefore that field of view is not appropriate for observation. FIG. 6(C) shows an example of a line profile of a field of view appropriate for observation. When a form 61 is present in a field of view 62, as shown in FIG. 6(A), the form appears as change in contrast as the electron beam passes through the specimen, whereby a line profile as shown in FIG. 6(C) is obtained. It is to be noted that only one measuring line 74 is drawn in the x-direction in FIG. 6(A); however, an arbitrary number of measuring lines may be drawn or the entire field of view may be scanned. It is also preferable that a plurality of measuring lines are drawn not only in the x-direction but also in the y-direction to obtain line profiles on these measuring lines.

Figure 7:
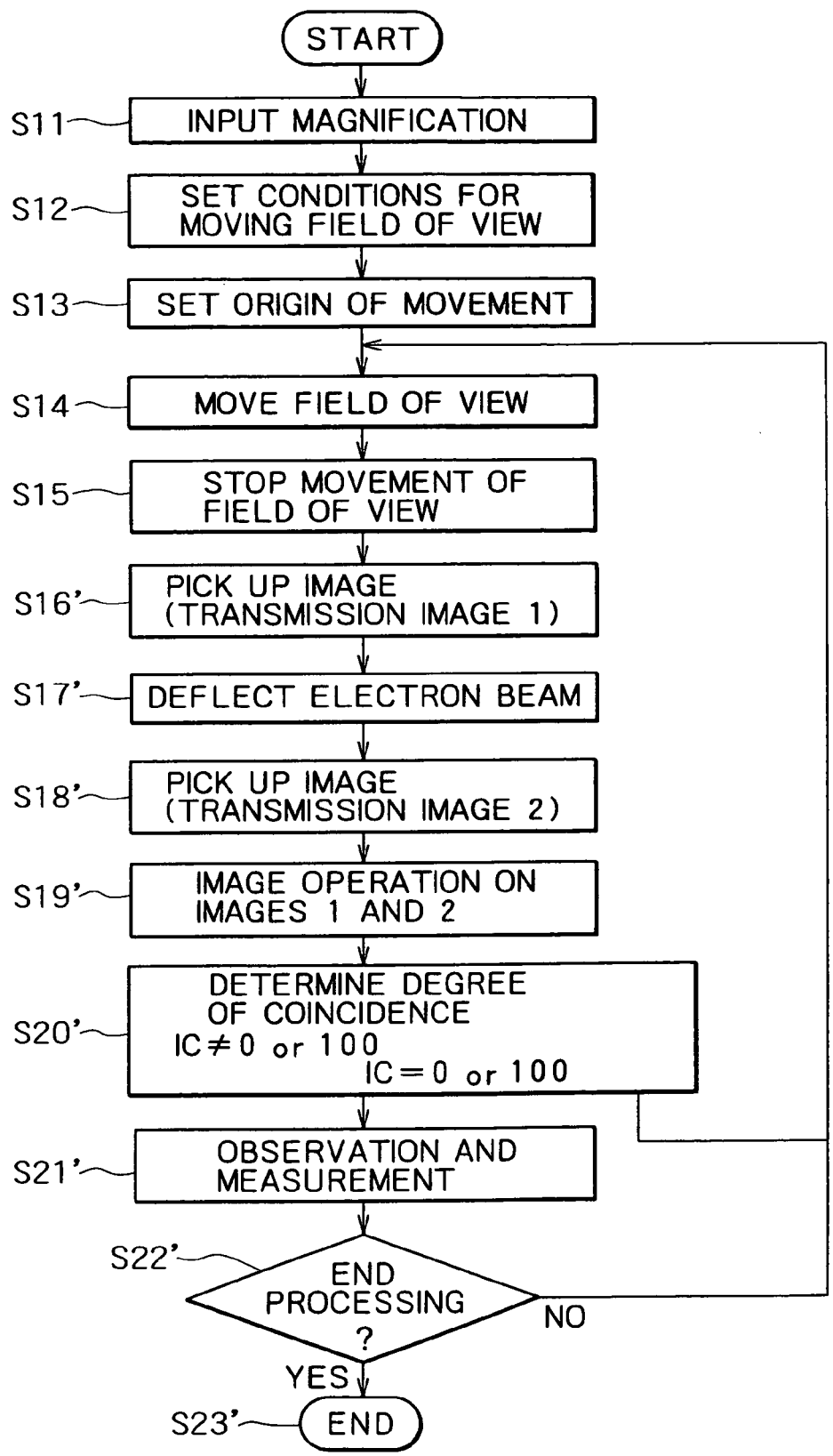
FIG. 7 is a flowchart illustrating a method for determining whether the field of view is appropriate for observation or search utilizing a correlation method.

FIG. 7 is a flowchart of assistance in explaining a method of determining a state of a field of view by the phase only correlation. A series of operations from a step 11 to a step 15 is the same as in FIG. 4. At a step 16', a magnified transmission image projected on the scintillator 16 is picked up by the TV camera 17. The magnified transmission image is stored in the storage unit as a transmission image 1. Next, at a step 17', the electron beam to be applied to the specimen is inclined by a deflection angle α, and at the next step 18', a magnified transmission image projected on the scintillator 16 is stored in the storage unit as a transmission image 2.

At a step 19', the transmission image 1 and the transmission image 2 are called up from the storage unit, and then the arithmetic unit 48 creates discrete Fourier transformation data of each of the images and thereby calculates a degree of coincidence between the transmission image 1 and the transmission image 2 by the phase only correlation method described by using the foregoing Equations 1 to 7.

At a step 20', whether the current field of view is on the mesh and therefore is not appropriate for field observation or search or whether the field of view is appropriate for field observation or search is determined by using the degree of image coincidence between the transmission image 1 and the transmission image 2 obtained at the step 19'. When the degree of coincidence between the transmission image 1 and the transmission image 2 is zero, it is determined that the field of view is not to be measured, and the processing returns to the step 14 to search for the next field of view. When the degree of coincidence between the transmission image 1 and the transmission image 2 is not zero nor 100, it is determined that the field of view is an appropriate region to be measured, and the processing proceeds to a step 21' (corresponding to the step 18 in FIG. 4). When the degree of coincidence between the transmission image 1 and the transmission image 2 is 100, it is determined that either the current field of view picks up an image on the mesh (FIG. 2(A)) or no form is present in the field of view because of breakage of the specimen or the like (FIG. 2(C)), and the processing returns to the step 14. In theory, the degree of coincidence of 100 indicates that two images completely coincide with each other; however, results of experiments have shown that the two images at the degree of coincidence of 100 are either deep black as shown in FIG. 2(A) or purely white as shown in FIG. 2(C). Thus, an image of a deep black field of view indicates that the image is taken on a specimen holding mesh 6, while an image of a purely white field of view indicates that no form is present in the field of view because of breakage of the specimen. Incidentally, a current apparatus takes about 0.9 to 1 seconds to perform calculation and make a determination for a single field of view by the phase only correlation method.

Description will next be made about how the degree of coincidence between two images each having a uniform tone throughout all of its pixels M×N becomes zero or 100. A function of an image 1 and a function of an image 2 are defined as f1(m, n) and f2(m, n), respectively, where m=0, 1, 2, . . . , M−1; n=0, 1, 2, . . . , N−1. The image 1 and the image 2 are uniform in brightness (gradation) throughout all of the pixels. Because of the above conditions, f2(m, n) is expressed as [Equation 13]. Hence, [Equation 14] and [Equation 15] are derived from [Equation 1] and [Equation 2].

$$f1(m, n) = f2(m, n) \quad \text{[Equation 13]}$$

$$F1(u, v) = \sum_{m=0}^{M-1} \sum_{n=0}^{N-1} f1(m, n) e^{-j2\pi(mu/M + nv/N)}$$
$$= A(u, v) e^{j\alpha(u,v)} \quad \text{[Equation 14]}$$

$$F2(u, v) = \sum_{m=0}^{M-1} \sum_{n=0}^{N-1} f1(m, n) e^{-j2\pi(mu/M + nv/N)}$$
$$= A(u, v) e^{j\alpha(u,v)} \quad \text{[Equation 15]}$$

When for the phase only correlation method, an amplitude component A(u, v) of [Equation 14] and [Equation 15] is set to be a constant of one, and [Equation 14] and [Equation 15] are set to be F1'(u, v) and F2'(u, v), respectively, [Equation 16] and [Equation 17] are obtained.

$$F1'(u, v) = e^{j\alpha(u,v)} \quad \text{[Equation 16]}$$

$$F2'(u, v) = e^{j\alpha(u,v)} \quad \text{[Equation 17]}$$

A synthetic phase image H(u, v) obtained by multiplying [Equation 16] by a complex conjugate of [Equation 17] is represented by [Equation 18].

$$H(u, v) = F1'(u, v)\{F2'(u, v)\}^*  \quad \text{[Equation 18]}$$
$$= e^{j(\alpha - \alpha)}$$
$$= 1$$

Then, a correlation index (correlation strength image) g(r, s) is expressed as [Equation 19] as a result of inverse Fourier transformation of [Equation 18].

$$g(r, s) = \sum_{m=0}^{M-1} \sum_{n=0}^{N-1} \{H(u, v)\} e^{j2\pi(ur/M + vs/N)} \quad \text{[Equation 19]}$$
$$= \begin{cases} MN & (r = 0, s = 0) \\ 0 & (r \neq 0, s \neq 0) \end{cases}$$

When an obtained value MN is normalized, a correlation index of 100 or zero is obtained.

Phase-amplitude correlation may also be used as a method of determining a state of a field of view. The flow of operation of the phase-amplitude correlation method is the same as that of the steps 16' to 20' in FIG. 7 using the phase only correlation method, but its principles of calculation are different from those of the phase only correlation method. A method of calculating a degree of image coincidence by using the phase-amplitude correlation method will be described in the following.

A magnified specimen transmission image is recorded in the storage unit as a transmission image 1 or f1(m, n) of M×N pixels, where m=0, 1, 2, . . . , M−1; n=0, 1, 2, . . . , N−1. Then, current is applied to the two upper electron beam deflecting coils 9 and 10, and a magnified specimen transmission image that is in the same field of view as the transmission image 1 and picked up by providing a certain inclining deflection angle a to the electron beam 73 applied to the specimen 14 is recorded in the storage unit as a transmission image 2 or f2(m, n) of M×N pixels.

Discrete Fourier images F1(u, v) and F2(u, v) of the transmission images f1(m, n) and f2(m, n) are defined by the foregoing [Equation 1] and [Equation 2], respectively. A synthetic image H12(u, v) represented by the following [Equation 20] is obtained by multiplying the discrete Fourier transformation image F1(u, v) of the transmission image 1 by a complex conjugate of the discrete Fourier transformation image F2(u, v) of the transmission image 2. A correlation strength image or a correlation index (degree of coincidence between the two images) g12(r, s) is expressed as the following [Equation 21] as a result of inverse Fourier transformation of the synthetic image H12(u, v).

$$H12(u, v) = F1(u, v) \cdot (F2(u, v)^*) \quad \text{[Equation 20]}$$
$$= A(u, v) B(u, v) e^{j(\alpha - \beta)}$$

$$g12(r, s) = \sum_{u=0}^{M-1} \sum_{v=0}^{N-1} (H12(u, v)) e^{j2\pi(ur/M + vs/N)} \quad \text{[Equation 21]}$$

The correlation strength image obtained by [Equation 21] is normalized. When an obtained value is zero, the two images are recognized to be completely different from each other, while when the obtained value is 100, the two images are recognized to be identical with each other. According to the phase-amplitude correlation method, as in the phase only correlation method, when a degree of coincidence of zero or 100 is obtained, it is determined that the current field of view is not appropriate for observation or search, and the processing returns to the step 14.

Returning to FIG. 4, at a step 18 (step 21' in FIG. 7), after it is determined that the current field of view is appropriate for observation or search, the magnified specimen transmission image 59 projected on the scintillator 16 is picked up by the TV camera 17, stored in the storage unit 47 as image data, and then displayed on the CRT 50 via a CRT driver 49 or used for composition analysis or the like. Also, coordinates of the selected field of view are stored in the storage unit 47.

Finally, at a step 19 in FIG. 4 (step 22' in FIG. 7), whether the processing flow is ended or not is determined on the basis of the conditions for moving the field of view set at the step 12, and when the processing flow is not to be ended, the processing returns to the step 14 to search for the next field of view.

By performing the operation described above, it is possible to automatically move or select the field of view, determine whether the selected field of view is appropriate for observation or not, and thereby efficiently observe only appropriate fields of view.

As an example of actual measurement, suppose that the specimen has a diameter of 2 mm, and the specimen is magnified to 100 mm in diameter at a transmission image magnification of 10000 to make a search. In this case, size of each field of view corresponds to about 10 μm on the plane of the specimen. Observation of the entire region of the specimen requires 40000 images to be picked up. However, in practice, since the specimen is held by the specimen holding mesh, images of the mesh are taken and therefore nothing can be seen in some fields of view, or the specimen is not present in some fields of view, as shown in FIG. 2. It can be estimated that the region of the mesh is about ½ of the entire search region of 2 mm in diameter, and the fields of view where the specimen is present constitute ⅒ of the entire region. Therefore, the fields of view appropriate for observation in the entire search region constitute about ¹⁄₂₀ of the 40000 fields of view for image pickup. According to the first embodiment, it is possible to automatically select only fields of view appropriate for observation, reduce the number of images to be picked up to ¹⁄₂₀, and accordingly reduce time required for search to about ¹⁄₂₀.

Figure 8:
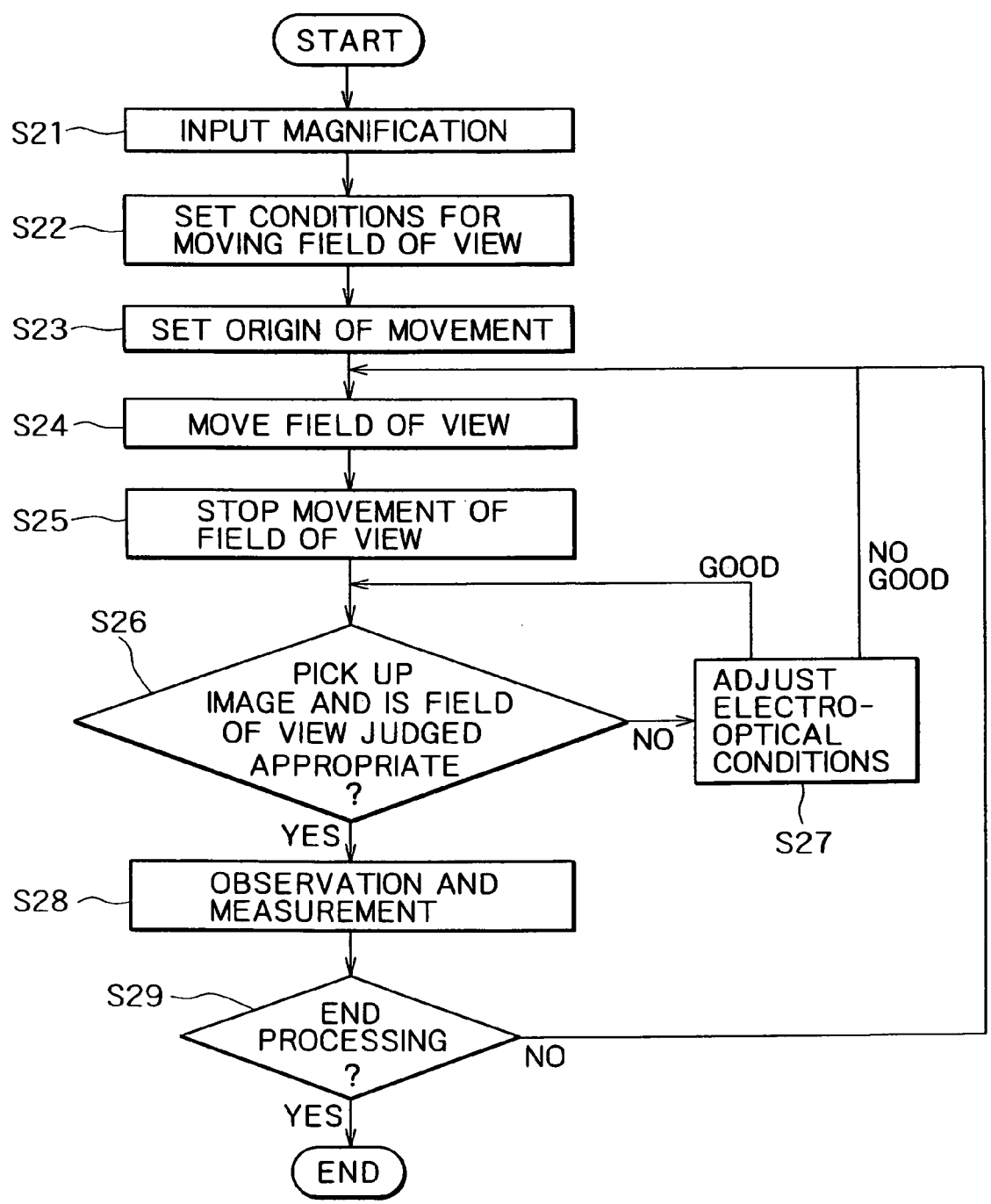
FIG. 8 is a flowchart illustrating a method for automatically examining and adjusting electro-optical conditions.

FIG. 8 is a flowchart of a second embodiment showing a method comprising the steps of automatically moving or selecting a field of view, determining whether the field of view is appropriate for observation or search, thereby efficiently observing or searching for only an appropriate field of view, and when it is determined that the field of view is not appropriate for observation, automatically adjusting electro-optical conditions.

In FIG. 8, input of magnification at a step 21, setting of conditions for moving a field of view at a step 22, setting of origin of movement at a step 23, moving the field of view at a step 24, and stopping the movement of the field of view at a step 25 are the same as in the steps 11 to 15 of FIG. 4, and therefore their repeated description will be omitted.

At a step 26, a magnified specimen transmission image 59 projected on the scintillator 16 is picked up by the TV camera 17, and then whether or not the current field of view is appropriate for observation or measurement is determined by using the line profile method, the phase only correlation method, or the phase-amplitude correlation method described above. When it is determined at the step 26 that the current field of view is appropriate for observation, the processing proceeds to a step 28 to measure, observe, or analyze the magnified specimen transmission image. When it is determined at the step 26 that the current field of view is not appropriate for observation, the processing proceeds to a step 27.

At the step 27, items that may be considered the factors in rendering the field of view inappropriate for observation are automatically examined to adjust electro-optical conditions. In this case, the following four items are examined and adjusted: (1) the electron beam, (2) lens conditions of the irradiation lenses, (3) electron beam current, and (4) an aperture or a position of a movable objective diaphragm. The item (1) is provided to examine a possibility that the electron beam is not emitted when the entire field of view is black. The item (2) is provided to examine a possibility that irradiation lens conditions of very low density of the specimen irradiation electron beam render the magnified transmission image undetectable with the sensitivity of the TV camera. The item (3) is provided to check for shortage of emission current or filament current. The item (4) is provided to examine a possibility that the aperture of the movable objective diaphragm is selected to be smaller than necessary, and thereby renders the field of view dark and undetectable by the TV camera, and a possibility that the aperture position of the movable diaphragm is not aligned with the optical axis of the electron beam.

Results of the four items are compared with preset values. When it is determined that the results do not satisfy the preset values, adjustment is made for each of the items to satisfy the preset value. When it is determined as a result of another image pickup that the current field of view is not appropriate for observation even though the results satisfy conditions of the above items, the processing returns to the step 24 to search for the next field of view. On the other hand, when the current field of view satisfies the preset values and it is determined that the field of view is appropriate for image pickup as a result of adjustment, the processing proceeds to the step 28 to observe, store, measure, or analyze the transmission image in that current field of view. Also, coordinates of the selected field of view are stored in the storage unit 47.

Finally, the processing proceeds to the step 29, and whether the processing flow is ended or not is determined on the basis of the conditions for moving the field of view set at the steps 22 and 23. When measurement is to be made again in accordance with the same processing flow, the processing returns to the step 24.

The operation described above enables automatic observation without omission by automatically moving or selecting a field of view, determining whether the selected field of view is appropriate for observation or not, and adjusting electro-optical conditions in an inappropriate field of view for a second determination process. According to the second embodiment, it is possible to minimize omission in search due to insufficient adjustment of electro-optical conditions and prevent human error, for example an error of not emitting the electron beam.

Figure 9:
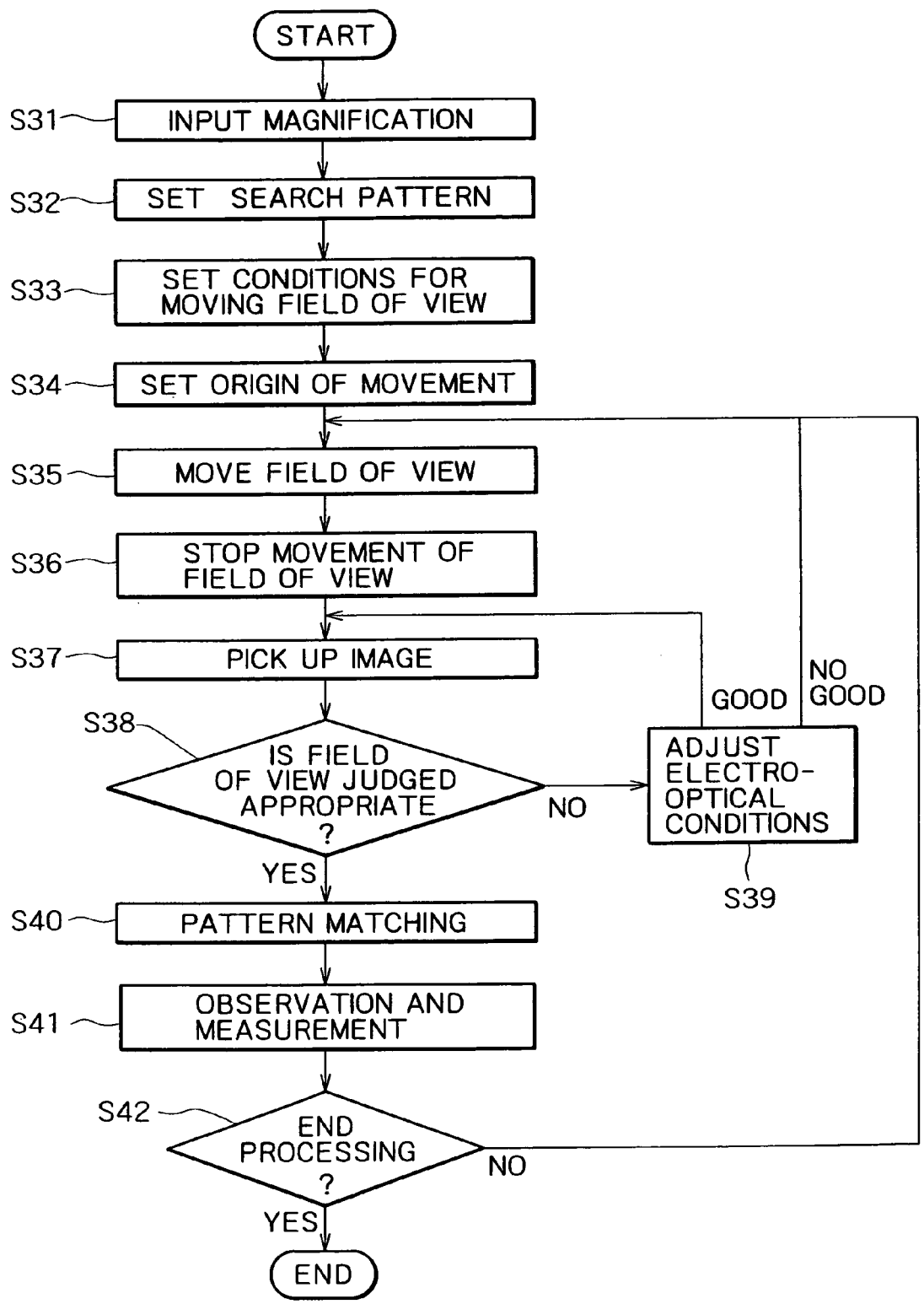
FIG. 9 is a flowchart illustrating a method for counting, displaying and storing the number of patterns that are the same as a preset search target pattern.

FIG. 9 is a flowchart of a third embodiment showing a method comprising the steps of automatically moving or selecting a field of view, presetting an arbitrary search target pattern similar to a search target form, determining whether the field of view has a brightness (gradation) inappropriate for observation or search, efficiently searching for only an appropriate field of view, automatically adjusting electro-optical conditions of the transmission electron microscope apparatus when it is determined that the field of view is inappropriate for observation or search, searching the field of view for a form having the same pattern as the search target pattern, and measuring, displaying and storing the number of forms obtained by the search.

Figure 10B:
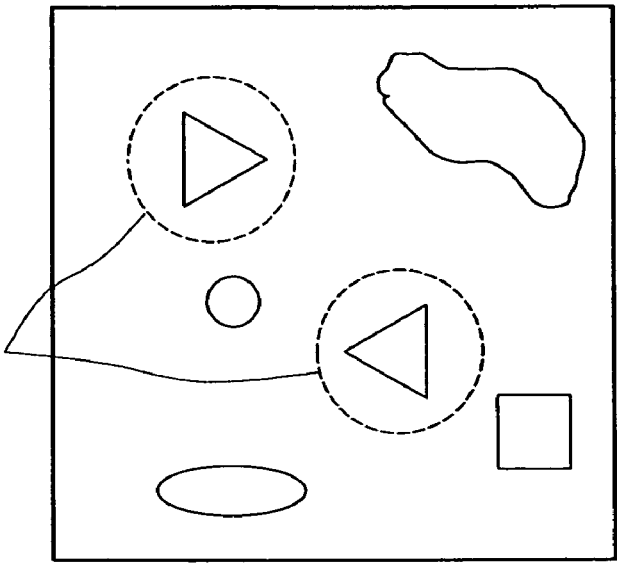
FIGS. 10(A) and 10(B) illustrates a search target pattern and an example of search target pattern extraction in a picked-up field of view.
Figure 10A:
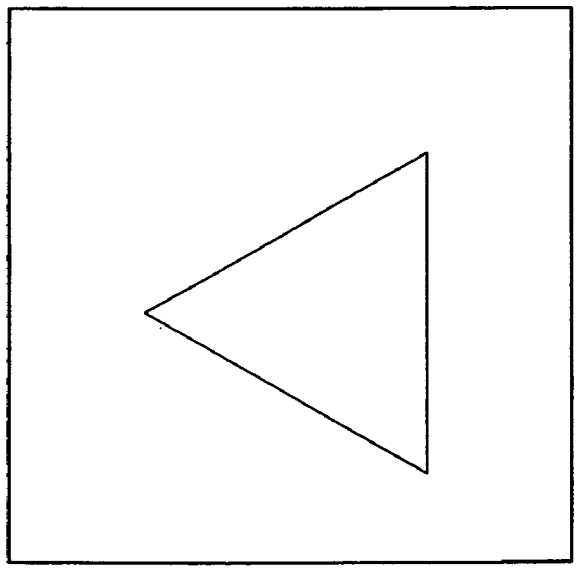

Suppose that in the third embodiment, a triangular form shown in FIG. 10(A), for example, is set as a search target pattern and a field of view is automatically moved, whereby a field of view taken as shown in FIG. 10(B) is obtained. A form having the same pattern as the triangle chosen as a search target pattern is automatically recognized and marked, and also the number of search target forms in the field of view is outputted for display.

At a step 31 in FIG. 9, a magnification is set to obtain a specimen transmission image. A magnification for a specimen transmission image is set, and lens currents that correspond to the magnification are outputted to the respective lens coils. At a step 32, a pattern (search target pattern) having the same shape as a search target form is set by using the keyboard 55 or the mouse 56. The search target pattern can be set by using conditions such as a range of angles between sides of the pattern, ellipticity, ratio in length between major and minor axes. The search target pattern may also be set by calling up a shape prestored in the storage unit.

Setting of conditions for moving a field of view at a step 33, setting of origin of field movement at a step 34, moving the field of view at a step 35, stopping the movement of the field of view at a step 36, and picking up a magnified specimen transmission image at a step 37 are the same as in the steps 12 to 16 of FIG. 4, and therefore their repeated description will be omitted. At a step 38, whether or not the current field of view is appropriate for observation or search is determined. Whether or not the current field of view is appropriate for observation or search may be determined by using the line profile method, the phase only correlation method, or the phase-amplitude correlation method described above. When it is determined that the field of view is appropriate for observation, the processing proceeds to a step 40. When it is determined that the field of view is not appropriate for observation, the processing proceeds to a step 39.

At the step 39, as in the step 27 in FIG. 8, factors that render the field of view inappropriate for observation are automatically examined, and then electro-optical conditions are adjusted. As described above, when it is determined as a result of a second image pickup that the current field of view is not appropriate for observation even though conditions of the check items are satisfied, the processing returns to the step 35 to search for the next field of view. On the other hand, when the current field of view satisfies the preset values and it is determined that the field of view is appropriate for image pickup as a result of adjustment, the processing proceeds to the step 40.

At the step 40, a form 61 judged to be the same as the search target pattern set at the step 32 is extracted from the field of view judged to be appropriate for measurement or observation. At the next step 41, the microprocessor 46 determines the number of search target forms extracted from the field of view taken at the step 37, and stores a result of the determination or an image of the field of view in the storage unit 47, or analyzes or takes a photograph of the search target forms. Also, coordinates of the selected field of view are stored in the storage unit 47.

A field of view where search target forms are detected is differentiated from a field of view where no search target forms are detected, for display on the display apparatus 50. For example, a field of view where search target forms are present is displayed in red, while a field of view where search target forms are not present is displayed in gray.

Figure 16:
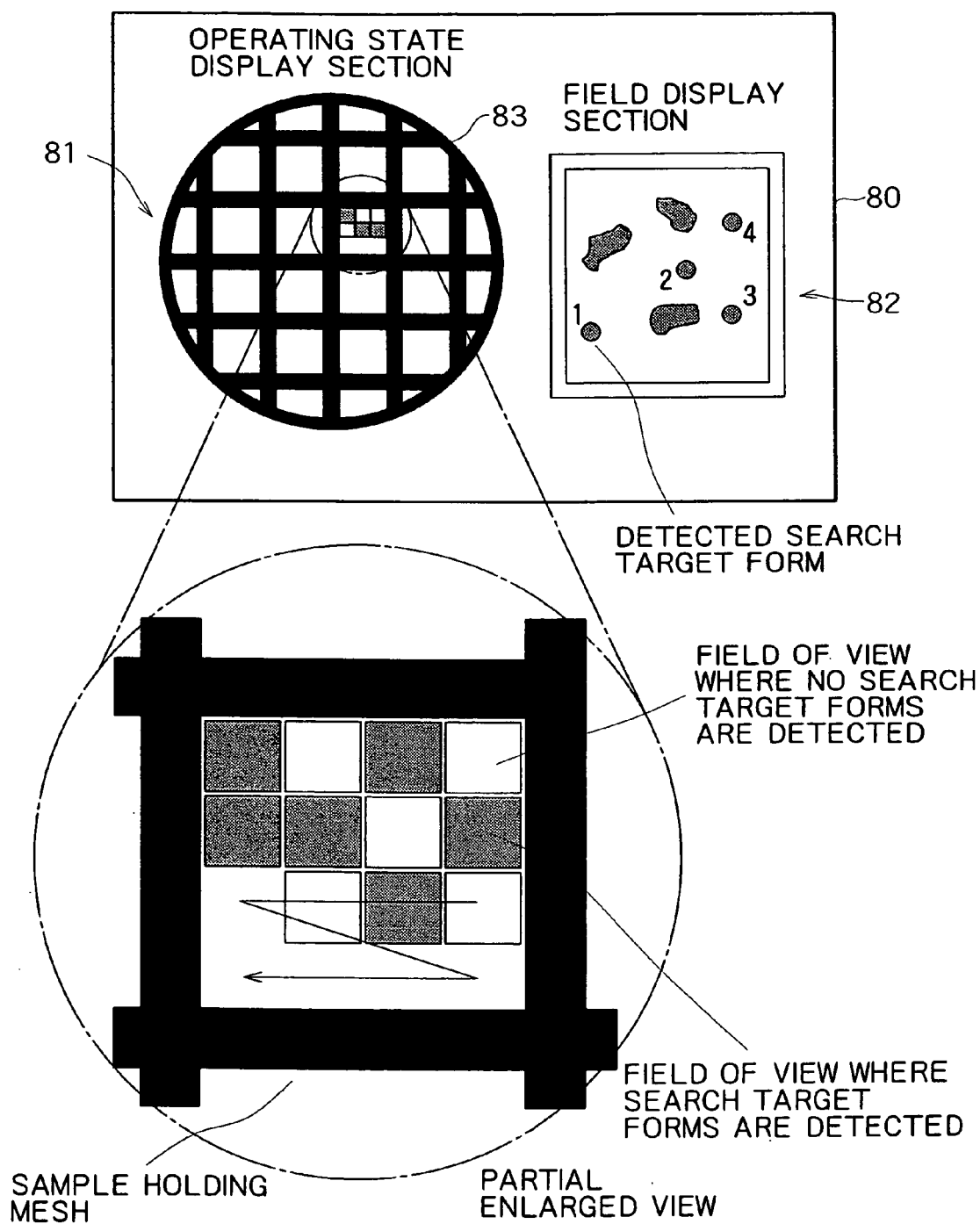
FIG. 16 illustrates a display on a display apparatus.

FIG. 16 is a schematic diagram showing an example of display on the display apparatus 50. In this example, an operating state display section 81 and a field display section 82 displaying a magnified image of a current observing field of view are placed side by side on a display screen 80 of the display apparatus 50. The operating state display section 81 displays a schematic diagram 83 of the specimen holding mesh 6, and at the same time schematically displays positional relation of each observing field of view to the specimen holding mesh. Also, when the operating state display section 81 displays fields of view, fields of view where search target forms are present are differentiated from fields of view where no search target forms are present by using different colors, as described above.

Returning to FIG. 9, finally whether the automatic search operation is repeated under the conditions for moving the field of view set at the steps 33 and 34 or whether the automatic search operation is ended is determined (step 42). When the automatic search operation is to be repeated, the processing returns to the step 35 to repeat the series of operations thus far described.

The operations described above allow the electron microscope that automatically moves or selects a field of view to search for only a field of view appropriate for observation, automatically adjust electro-optical conditions for an inappropriate field of view having an insufficient brightness so that the field of view can be used for observation, and automatically search for search target forms. In addition, the electron microscope does not carry out a search on the mesh or in a section in which the specimen is broken, where it is obvious that the specimen cannot be seen in the field of view.

According to the third embodiment, as in the previous embodiments, a search for target forms, which has been conventionally carried out by the operator after taking photographs, can be made instantly and simultaneously with image pickup. In addition, since only fields of view appropriate for observation are automatically extracted, it results in an improved efficiency as compared with a method that picks up images of the entire region of the specimen to search for target forms.

Suppose that a specimen 2 mm in diameter is magnified to 100 mm in diameter at a transmission image magnification of 10000, photographs are taken of all fields of view on the specimen holding mesh, and the photographs taken are searched for target forms by manpower. Then, since it is necessary to pick up a total of 40000 images, the search requires about 670 hours, assuming that it takes one minute to search a single photograph for target forms. According to the third embodiment, it is possible to search for target structural forms by automatically extracting only the fields of view that can be used for observation of the specimen and therefore are not in sections where the specimen is broken or on the mesh. Since fields of view appropriate for observation constitute 1/20 of the entire region of the specimen and a current apparatus takes about one second to search a single field of view for target forms, the time required to search for forms is dramatically reduced.

By adjusting electro-optical conditions, it is possible to minimize omission in search due to insufficient adjustment of electro-optical conditions and prevent human error, for example an error of not emitting the electron beam. Also, it is possible to control change in electro-optical conditions with time that might result from automatic observing operation over a long period of time, and to thereby keep observing conditions stable. In addition, since fields of view including target forms are clearly distinguished by using a different color and coordinates of the fields of view are stored in the storage unit, it is easy to observe or analyze the fields of view again after completion of the search operation. When observation is to be made again, a displayed field of view is selected, and on the basis of coordinates stored in association with the field of view, the specimen stage 13 is driven or the target field of view is moved by the electron beam deflector. Then, it is possible to obtain a magnified transmission image of a desired field of view instantly.

Figure 11:
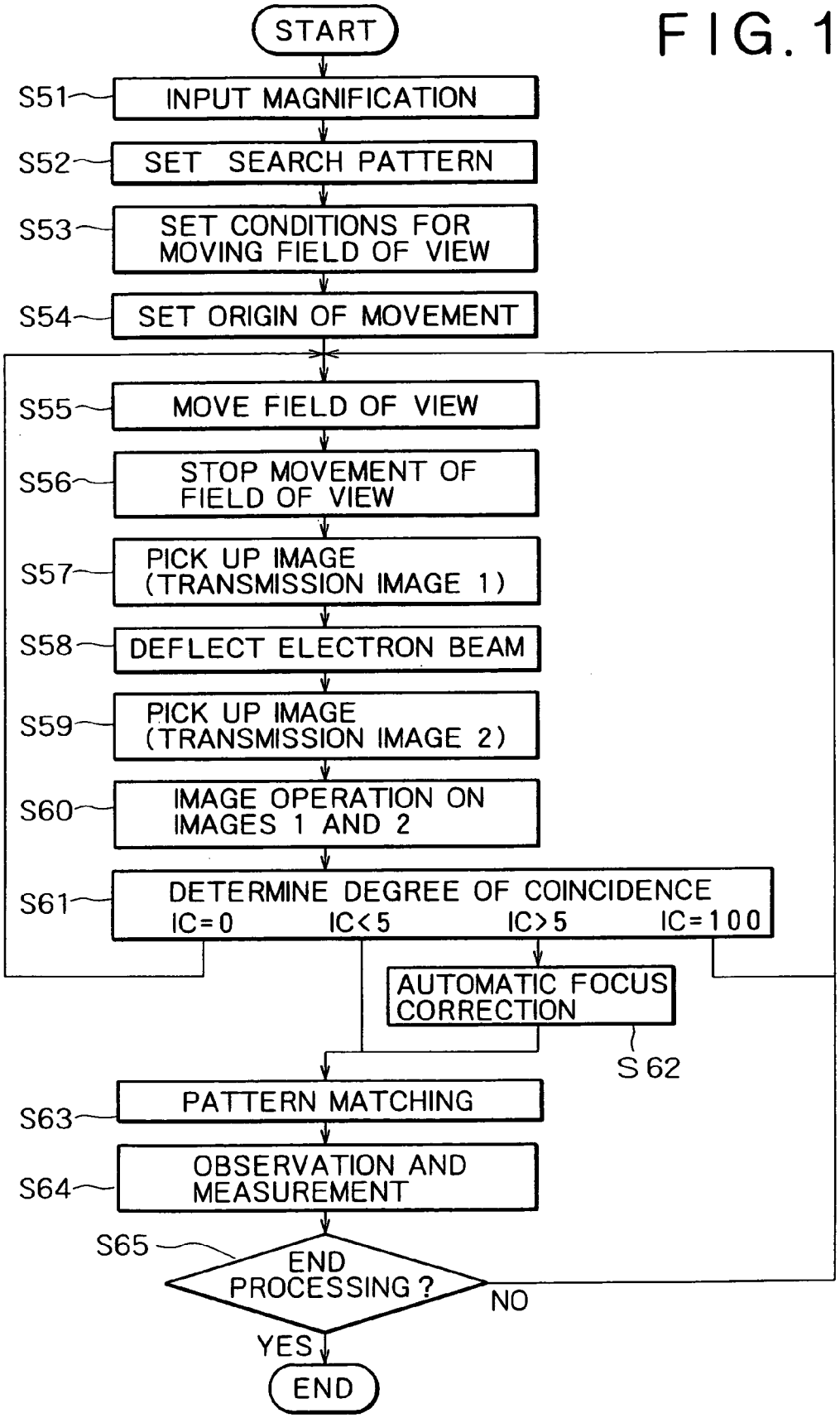
FIG. 11 is a flowchart illustrating a method for automatically correcting focus, and searching for a preset form pattern.

FIG. 11 is a flowchart of a fourth embodiment showing a method comprising the steps of automatically moving or selecting a field of view, determining whether the current field of view is appropriate for observation or search, automatically correcting focus, and automatically searching for a form pattern having an arbitrary preset search target shape.

In FIG. 11, setting of a magnification at a step 51, setting of a search target pattern at a step 52, setting of conditions for automatically moving a field of view at a step 53, setting of origin of field movement at a step 54, moving the field of view at a step 55, and stopping the movement of the field of view at a step 56 are the same as in the steps 31 to 36 of FIG. 9, and therefore their repeated description will be omitted.

In steps 57 to 60, a correlation between two images is calculated by discrete Fourier transformation using only the phase components of the two images. First, at the step 57, a magnified specimen transmission image 59 obtained by the electron beam 73, which perpendicularly falls on the specimen along the electron beam optical axis 72, is projected on the scintillator 16 and then picked up by the TV camera 17. This transmission image is set to be a transmission image 1. At the next step 58, the two electron beam deflecting coils over the specimen provide the electron beam falling on the specimen with an arbitrary inclining deflection angle with respect to the electron beam optical axis. Then, a magnified specimen transmission image that is obtained by the inclined electron beam and in the same field of view as the transmission image 1 on the scintillator is picked up by the TV camera as a transmission image 2. At the step 60, an index of correlation (degree of coincidence) between the transmission image 1 and the transmission image 2 is obtained by discrete Fourier transformation using only the phase components of the two images. The principles of the calculation have been illustrated earlier by using Equations 1 to 7.

On the basis of the correlation index calculated at the step 60, whether or not the current field of view has a brightness appropriate for search is determined at a step 61. After the result of the determination is obtained, the processing is branched off into four ways to be taken according to the value of the correlation index.

(1) When the correlation index is zero, it is determined that the current field of view cannot be used for search or measurement, and the processing returns to the step 55 to search for another field of view.

(2) When the correlation index is 100, it is determined that the current field of view is on the specimen holding mesh, or the specimen is not present in the field of view because of breakage of the specimen or the like and therefore a magnified specimen transmission image cannot be obtained properly. The processing returns to the step 55 to search for another field of view.

(3) When the correlation index is more than a preset reference value and is not 100, it is determined that the current field of view is appropriate for measurement or search, and the processing proceeds to the next step 62. The reference value of the correlation index is preset as a threshold value necessary to satisfactorily perform automatic focus correction for a magnified specimen transmission image. The correlation index varies depending on the amount of displacement between the two transmission images, contrast between forms and background of the transmission images, S/N of the images and the like. The threshold value in the flowchart of FIG. 11 is set at five, which is a value obtained by experiment. At the step 62, automatic focus correction is made according to the method illustrated by Equations 8 to 12. After completion of the automatic focus correction, the processing proceeds to a step 63.

(4) When the correlation index is less than the reference value and is not zero, it is determined that the current field of view is appropriate for measurement or search but exact automatic focus correction cannot be ensured. The processing proceeds to the step 63.

At the step 63, the search target pattern having an arbitrary shape set at the step 52 is called up from the storage unit, and then the microprocessor makes a search to determine whether the desired form pattern is present in the current field of view. At the step 64, the number of forms judged to have the same form pattern as the search target pattern as a result of search is counted and the image is registered, displayed, or analyzed. Also, coordinates of the selected field of view are stored in the storage unit 47.

A field of view where search target forms are detected is differentiated from a field of view where no search target forms are detected, for display on the display apparatus. For example, a field of view where search target forms are present is displayed in red, while a field of view where search target forms are not present is displayed in gray. Also, coordinates of each of the fields of view including search target forms are displayed on the display apparatus, and are at the same time stored in the storage unit.

Finally, at a step 65, whether automatic field search is to be continued or not is determined. When search is to be made again, the processing returns to the step 55 to repeat the series of operations. When search is not to be made again, the processing is ended.

As in the case of the third embodiment, the fourth embodiment allows the electron microscope automatically moving a field of view and searching for target structure to search for only a field of view appropriate for observation. According to a conventional automatic search method, it is not possible to separate fields of view appropriate for observation from fields of view inappropriate for observation. On the other hand, when a search for target structure is made in only the fields of view appropriate for observation, as in the fourth embodiment, the time required for the search is greatly reduced. In addition, lens focal length might be changed in each of the fields of view because of breakage or warping of the specimen, but since automatic focus correction is made when the field of view is moved, it is possible to prevent a decrease in pattern matching accuracy due to blurred images resulting from defocus. Moreover, when a search has been made once and a field of view including a target structure is to be observed again, it is possible to obtain a magnified transmission image in the target field of view instantly by selecting coordinates stored in the storage unit and thereby driving the specimen stage 13 or using the electron beam deflector.

Figure 12:
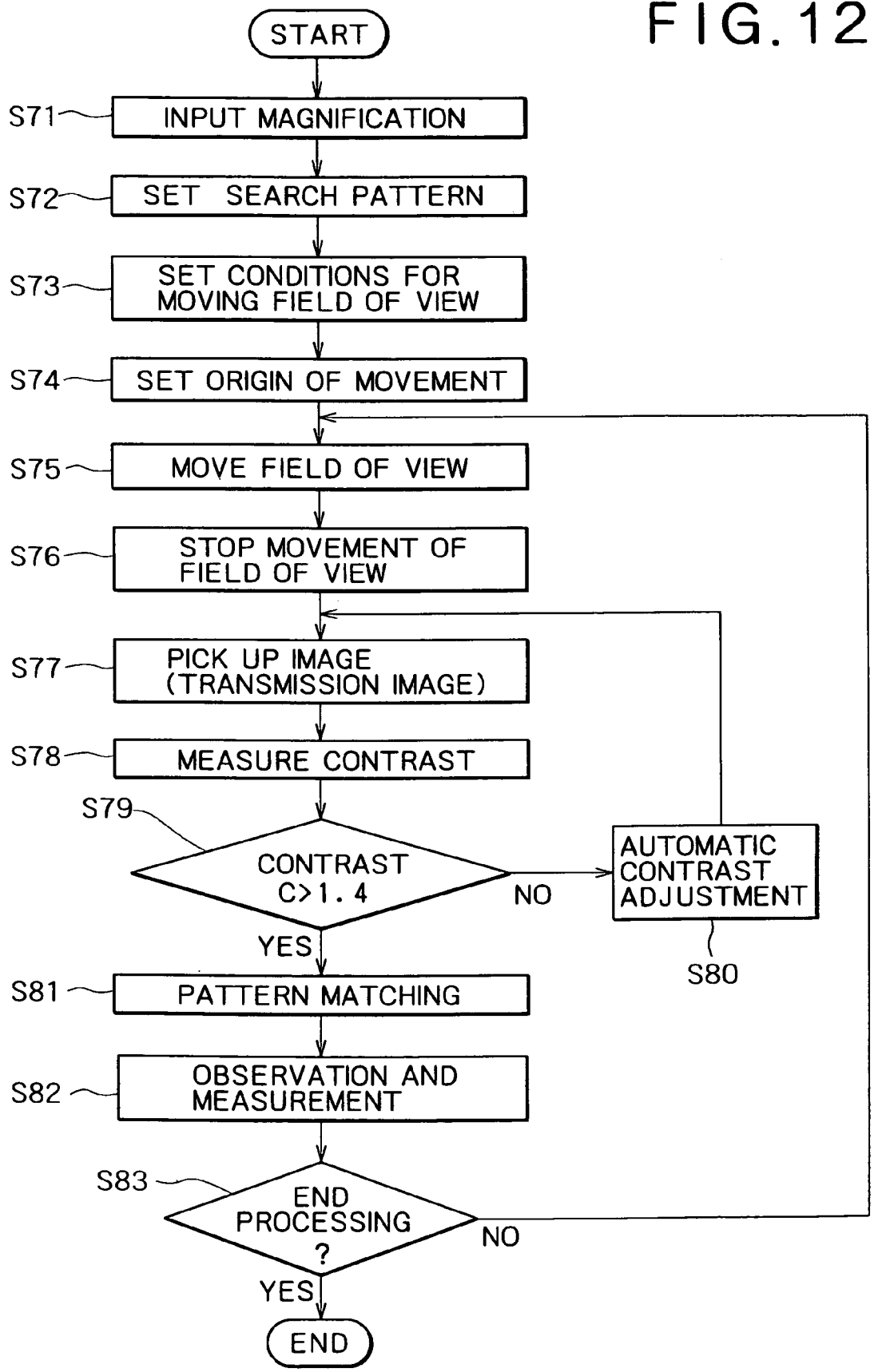
FIG. 12 is a flowchart illustrating a method of matching a search target pattern.

FIG. 12 is a flowchart of a fifth embodiment showing a method of increasing accuracy in automatic search and thereby improving reliability in the electron microscope that automatically moves or selects a field of view and automatically searches for a form matching a search target pattern of an arbitrary shape.

In FIG. 12, setting of a magnification at a step 71, setting of a search target pattern at a step 72, setting of conditions for automatically moving a field of view at a step 73, setting of origin of field movement at a step 74, moving the field of view at a step 75, and stopping the movement of the field of view at a step 76 are the same as in the steps 31 to 36 of FIG. 9 or in the steps 51 to 56 of FIG. 11, and therefore their repeated description will be omitted.

At a step 77, a magnified specimen transmission image 59 in a selected field of view projected on the scintillator 16 is taken by the TV camera 17. The taken transmission image is stored in the storage unit. In contrast measurement at a step 78, the taken image is called up from the storage unit, and then the microprocessor creates line profiles of signal intensity (brightness). Line profiles corresponding to a specimen transmission image are shown in FIGS. 13(1), 13(2), and 13(3).

Ratio in signal intensity (brightness) between a background 65 and a form 61 in the specimen in the specimen transmission image (left side) of FIG. 13 is expressed as a contrast C. When a measuring line 74 is drawn so as to cross forms in the field of view and a signal intensity distribution on the measuring line is graphed, a line profile as shown on the right side of FIG. 13 is obtained (the axis of abscissas denotes picture elements [pixel] and the axis of ordinates denotes signal intensity (brightness) [arb.u]). When signal intensity of the background is set to be $I_0$ and signal intensity of the form is set to be $I_1$, the contrast C is defined by the following [Equation 22].

$$C = I_1/I_0 \quad \text{[Equation 22]}$$

FIGS. 13(1), 13(2), and 13(3) show specimen transmission images obtained by changing the contrast experimentally, each of which includes a total of 34 search target forms. Numerals provided in the transmission images denote forms 75 that are judged to be the same as the search target pattern as a result of search. At a contrast C=1.1 in FIG. 13(1), no forms can be detected. At a contrast C=1.2 in FIG. 13(2), 25 of the 34 forms can be detected. At a contrast C=1.6 in FIG. 13(3), all of the 34 forms can be detected. Thus, the number of searchable forms varies depending on the contrast of the specimen transmission image. The numbers of forms detected are shown in Table 1.

TABLE 1

| Contrast C | Number of particles detected | Detection accuracy (%) |
|---|---|---|
| 2.0 | 34 | 100 |
| 1.6 | 34 | 100 |
| 1.5 | 34 | 100 |
| 1.3 | 32 | 94 |
| 1.2 | 25 | 75 |
| 1.1 | 0 | 0 |

Figure 14:
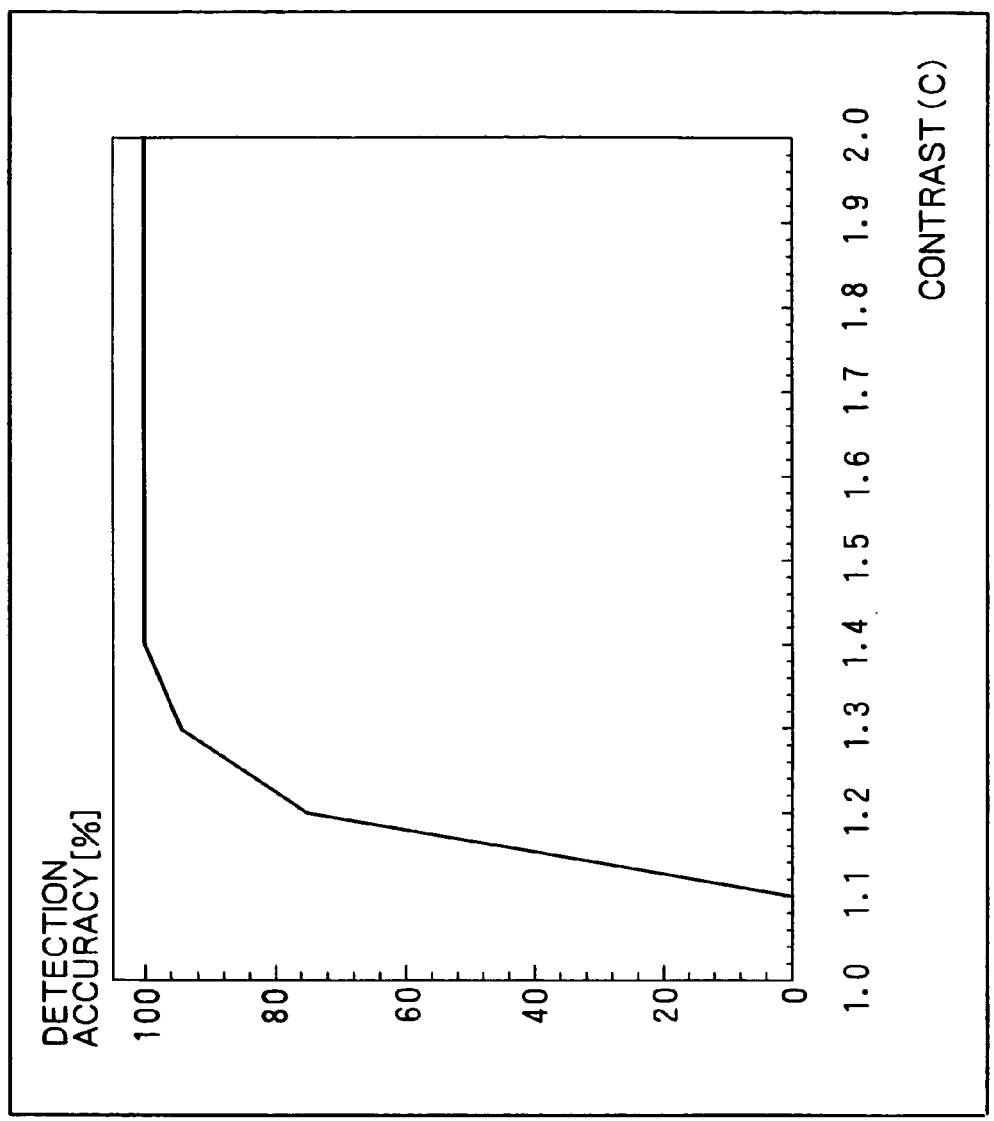
FIG. 14 is a graph illustrating a change in accuracy in detection of a search target pattern with respect to change in contrast.

When percentage of the number of particles detected to the total number of forms of 34 is defined as detection accuracy, then detection accuracies for different contrasts are graphed as shown in FIG. 14. As is understood from FIG. 14, the detection accuracy increases as the contrast is enhanced. A difference between signal intensity of the form and noise in the background signal or statistical variation is small in a low-contrast image, and therefore the signal intensity of the form and noise in the background signal or statistical variation cannot be separated from each other, thus decreasing search accuracy.

In order to increase the detection accuracy and thereby improve reliability in measurement, steps 78 to 80 are carried out. A relation between contrast and detection accuracy obtained on the basis of experimental results as shown in FIG. 14 is prestored in the ROM. At a step 79, whether a measured contrast allows detection accuracy to become 100 or not is determined. According to the flowchart of FIG. 12, C>1.4 is used as a reference in such determination. At the step 79, when C>1.4, it is determined that a detection accuracy of 100% can be ensured, and the processing proceeds to a step 81. When C≦1.4, it is determined that the detection accuracy is insufficient, and the processing proceeds to the step 80 to make contrast adjustment.

At the step 80, electro-optical conditions are adjusted to enhance the contrast. The transmission electron microscope has the following four methods (1) to (4) for enhancing contrast: (1) to reduce the aperture of the movable objective diaphragm, (2) to provide an appropriate amount of defocusing, (3) to subject the taken image to image processing by the microprocessor, and (4) to decrease the accelerating voltage. The methods (1) and (2) will be described and detailed description of the methods (3) and (4) will be omitted here.

The method (1) utilizes the principle that when the aperture of the movable objective diaphragm is reduced to prevent undesired scattering of the electron beam, an image of pure information on the specimen is formed, and thereby the contrast of the image is enhanced. The microprocessor 46 operates a movable diaphragm driving mechanism 31 connected to the movable objective diaphragm 15 via a driving mechanism driver 32 so as to make the aperture of the movable objective diaphragm 15 smaller for enhanced contrast.

The method (2) utilizes the principle of Fresnel diffraction. The Fresnel diffraction produces a fringe (Fresnel fringe) in an electron microscope image when defocusing occurs. The Fresnel fringe enhances the contrast between the forms and the background. A method of moderately defocusing an image is commonly used as an electron microscope photographic technique.

At the step 80, processing for improving the contrast is performed by any one of the methods (1) to (4). For example, an appropriate amount of defocusing corresponding to the magnification is provided to enhance the contrast. After the contrast is adjusted at the step 80, the processing returns to the step 77 to determine whether a proper contrast is obtained or not again.

When it is determined at the step 79 that a proper contrast is obtained, the transmission image in the field of view is searched for a form pattern that matches the search target pattern preset at the step 72. At the next step 82, the number of forms judged to have the same form pattern as the search target pattern is counted and the image is registered, displayed, or analyzed. Also, coordinates of the selected field of view are stored in the storage unit 47.

Finally, at a step 83, whether automatic field search is to be continued or not is determined. When search operation is to be performed again, the processing returns to the step 75 to repeat the series of operations. When search is not to be made again, the processing is ended.

Accuracy in pattern matching search, in which the electron microscope automatically moving or selecting a field of view searches for fields of view including a target structural pattern, depends on the contrast of a magnified specimen transmission image, as described with reference to FIGS. 13(1), 13(2), and 13(3). By measuring and automatically adjusting the contrast of a transmission image, as in the fifth embodiment, it is possible to increase accuracy in search for a target structure. Because of nonuniformity in staining during specimen preparation, the contrast of all fields of view of even the same specimen is not necessarily constant. Thus, by measuring and automatically adjusting the contrast of each field of view, it is possible to increase search accuracy.

Figure 15:
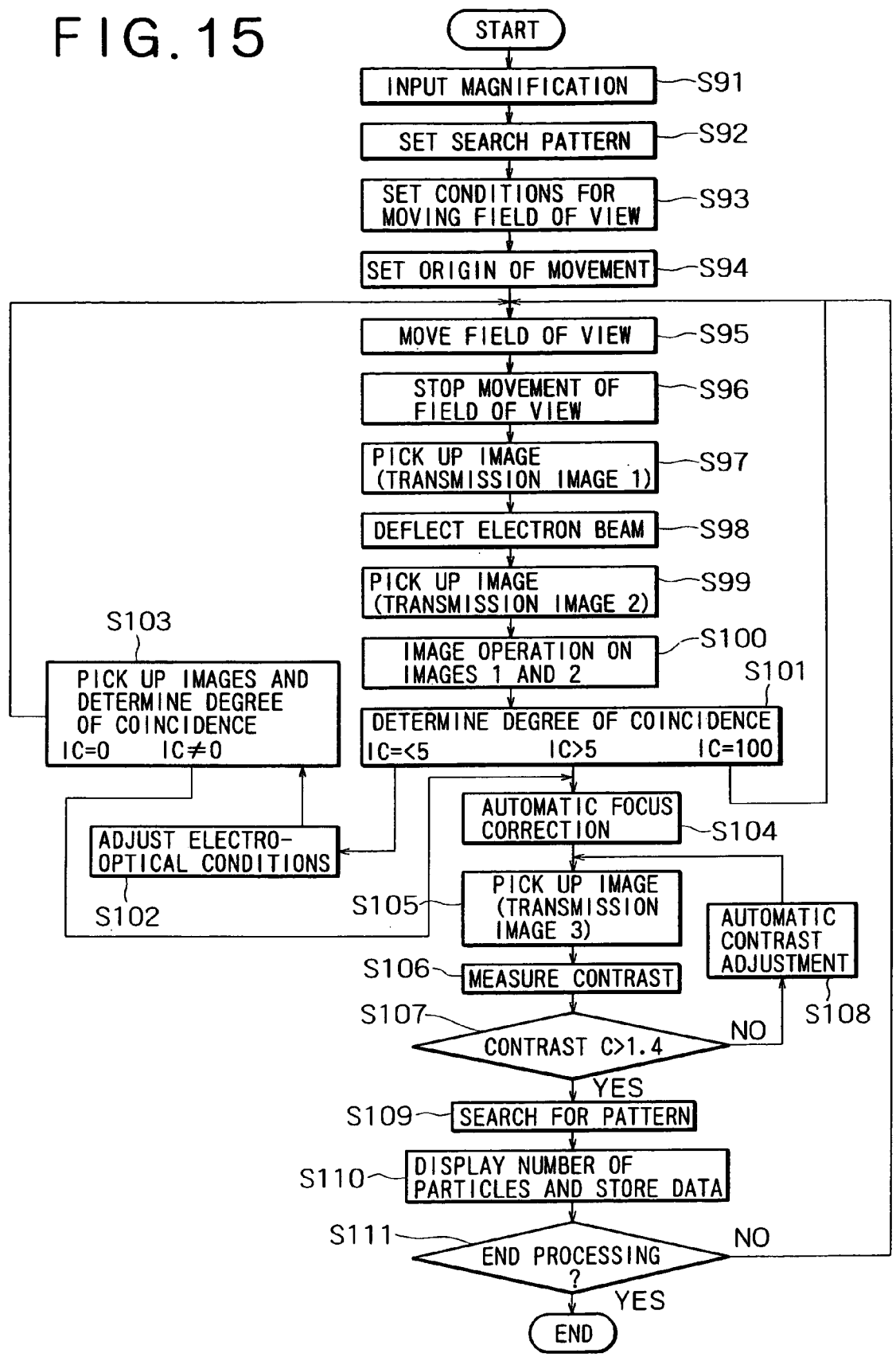
FIG. 15 is a flowchart illustrating a method of another embodiment of the present invention.

FIG. 15 is a flowchart of a sixth embodiment showing a method for the electron microscope that automatically moves or selects a field of view and automatically searches for a form matching a search target pattern of an arbitrary shape, the method including the steps of making automatic focus correction and automatic contrast adjustment of a specimen transmission image, and thereby searching for desired forms with high accuracy and high detection efficiency. An image computation of the sixth embodiment employs an arithmetic method for obtaining a phase-component-only phase-amplitude correlation from discrete Fourier transformation of transmission images.

In FIG. 15, operations from a step 91 to a step 96 are the same as those in the steps 31 to 36 shown in FIG. 9, and therefore their detailed description will be omitted.

At steps 97 to 101, the same operations as in the steps 57 to 61 of FIG. 11 are performed. At the step 97, a magnified specimen transmission image obtained by the electron beam, which perpendicularly falls on the specimen along the electron beam optical axis, is picked up and recorded as a transmission image 1. At the step 98, the two electron beam deflecting coils over the specimen provide the electron beam falling on the specimen with a certain inclining deflection angle with respect to the electron beam optical axis. Then, a magnified specimen transmission image that is obtained by the deflected electron beam and in the same field of view as the transmission image 1 is picked up and recorded as a transmission image 2. At the step 100, an index of correlation (degree of coincidence) between the transmission image 1 and the transmission image 2 is obtained by discrete Fourier transformation using only the phase components of the two images. The principles of the calculation have been illustrated earlier by using Equations 1 to 7. By using the arithmetic result obtained at the step 100, whether or not the current field of view is appropriate for search is determined at a step 101. After the result of the determination is obtained, the processing is branched off into three ways to be taken according to the value of the correlation index.

(1) When the correlation index is zero or does not satisfy an equation of a predetermined threshold value, the processing proceeds to a step 102. In the sixth embodiment, the threshold value is set at five, which is a value obtained by experiment.

(2) When the correlation index is 100, it is determined that either the current field of view is on the specimen holding mesh or the specimen is not present in the field of view because of breakage of the specimen or the like. The processing returns to the step 95 to search for another field of view.

(3) When the correlation index is more than the arbitrarily set threshold voltage and is not 100, the processing proceeds to a step 104.

At the step 102, factors that cause the field of view to be judged inappropriate for observation are automatically examined to adjust electro-optical conditions. As in the step 27 in the flowchart of FIG. 8 described in the second embodiment, the following items are examined and adjusted: (1) emission of the electron beam, (2) lens conditions of the irradiation lenses, (3) electron beam current, and (4) the aperture or the aperture position of the movable objective diaphragm. Then, at a step 103, transmission images are picked up, and a degree of coincidence between the images is calculated from the phase components of the discrete Fourier images, as in the steps 97 to 100. At the step 103, when the degree of coincidence is zero, it is determined that the field of view is not appropriate for observation, and the processing returns to the step 95. When the degree of coincidence is not zero, it is determined that the field of view can be used for observation, and the processing proceeds to the step 104.

At the step 104, current of the objective lens or height of the specimen stage is adjusted by using a result of a positional displacement calculation performed in the image computation to thereby effect automatic focus correction. At a step 105, a magnified specimen transmission image 59 projected on the scintillator 16 is picked up as a transmission image 3 by the TV camera 17, and stored in the storage unit 47. The focus of the transmission image 3 is corrected and therefore the specimen transmission image is in focus.

As described with reference to FIGS. 13(1), 13(2), and 13(3) and FIG. 14, accuracy in automatic search for forms is decreased unless a sufficient contrast of a magnified specimen transmission image is ensured. Therefore, in steps 106 to 108, the transmission image 3 taken at the step 105 is measured to determine whether the transmission image 3 has a contrast sufficient to obtain a satisfactory search accuracy, and accordingly the contrast is automatically adjusted. At the step 106, the transmission image 3 is called up from the storage unit, and then the microprocessor 46 creates a line profile of signal intensity (brightness). The contrast of the transmission image is calculated from the line profile. Then, whether or not the contrast allows detection accuracy to become 100 is determined by using the relation between contrast and detection accuracy in FIG. 14 obtained on the basis of experimental results and prestored in the ROM 58. Since the detection accuracy reaches 100 at a contrast of 1.4 or higher, a threshold value of determination is set at 1.4 in the sixth embodiment. At the step 107, when the contrast is 1.4 or higher, the processing proceeds to a step 109. On the other hand, when the contrast is below 1.4, the processing proceeds to the step 108.

At the step 108, as in the step 80 of FIG. 12, the contrast is adjusted. The four methods for enhancing the contrast are as follows: (1) to reduce the aperture of the movable objective diaphragm, (2) to provide an appropriate amount of defocusing, (3) to subject the taken image to image processing by the microprocessor, and (4) to decrease the accelerating voltage. In this case, an appropriate amount of defocusing corresponding to the observing magnification is provided to the in-focus image obtained by automatic focus correction at the step 104 to thereby enhance the contrast of the image. At the step 108, defocusing data preset so as to correspond to observing magnifications and stored in the ROM 58 is called up, lens data to be supplied to the objective lens coil 4 is outputted to the DAC 37, and then an analog signal is supplied to the lens exciting power supply 20 to thereby output lens current. After an appropriate amount of defocusing is provided at the step 108, the processing returns to the step 105, where a magnified specimen transmission image having an enhanced contrast is picked up and stored in the storage unit.

When it is determined that the contrast in signal intensity between the background and the form of the transmission image 3 is 1.4 or higher, the processing proceeds to the step 109 to automatically search the field of view for a form having a pattern that matches the search target pattern set at the step 92. The search target pattern is called up from the storage unit, and then the microprocessor searches the field of view for a form having the same pattern as the search target pattern. Forms judged to have the same pattern as the search target pattern are marked, the number of such forms is counted, and the transmission image is registered in the storage unit and displayed on the display apparatus. The search target forms are subjected to composition analysis as required (step 110). Also, coordinates of the selected field of view are stored in the storage unit 47.

Finally, at a step 111, whether automatic field search is to be continued or not is determined. When search operation is to be performed again to search for the next field of view, the processing returns to the step 95 to repeat the series of flow processes from the step 95 down. When the search is not to be made again, the processing is ended.

The electron microscope automatically moving or selecting a field of view takes several hours or more to search a single specimen for a target structure, depending on the observing magnification of the electron microscope. If the search operation is performed for the several hours unattended, there is a possibility that the magnified transmission image may lose a sufficient brightness because of ending life of the filament of the electron gun or an abnormal current, for example. Also, the unattended and high-speed search operation makes it impossible to make adjustments by intervention of the operator during the automatic search operation.

The sixth embodiment incorporates and combines all the features of the first to fifth embodiments. A conventional electron microscope automatically moving or selecting a field of view takes photographs of fields of view on the mesh or in a section in which the specimen is broken, where obviously no structure is present, to search for a target structure pattern. On the other hand, the electron microscope of the sixth embodiment skips search for a structure pattern in fields of view where no structure should be present or observation is not possible, thereby making it possible to complete the search operation in about 1/20 of the search time of the conventional electron microscope. In addition, it is possible to automatically adjust electro-optical conditions that are changed with time by repeated search operations over a long time. With the electron microscope of the sixth embodiment automatically searching a field of view, it is possible to automatically correct objective lens focal length changed by breakage or warping of part of the specimen, and to automatically correct contrast changed by nonuniformity in specimen staining. Thus, it is possible to search for target structures with high accuracy and high efficiency. Furthermore, coordinates and an image where a target structure is present are recorded and stored in the storage unit, and therefore when the magnified specimen transmission image is to be observed, taken, or analyzed again after specimen search operation, it is possible to obtain instant access to the target specimen position.

Hence, specimen search operation using an electron microscope, which has conventionally been complex and required considerable labor and time of the operator, can be performed automatically with high accuracy and in a short time. Accordingly, the present invention provides a method of observing a specimen in a field of view of an electron microscope comprising the acts of illuminating the specimen with an electron beam having a first angle and forming a first transmission image of the specimen in the field of view and adjusting the electron beam to a second angle and forming a second transmission image of the specimen in the field of view and calculating a degree of coincidence between the first and second transmission images.

Although the invention has been described above in connection with exemplary embodiments, it is apparent that many modifications and substitutions can be made without departing from the spirit or scope of the invention. Accordingly, the invention is not to be considered as limited by the foregoing description, but is only limited by the scope of the appended claims.

What is claimed as new and desired to be protected by Letters Patent of the United States is:

1. An electron microscope comprising:
a support for supporting a specimen;
a deflector for deflecting an electron beam to the specimen to form images;
an image pickup device for obtaining the images; and
a processor coupled to the image pickup device being programmed for observing the specimen in a field of view of the electron microscope, said programming comprising the act of:
calculating a degree of coincidence of images obtained by differential electro-optical conditions of the electron microscope;
determining whether the image of the field of view is suitable or not for an observation based on calculated degree; and
moving the field of view to a next position when the image of the field of view is determined to be not suitable.

2. An electron microscope comprising:
a support for supporting a specimen;
a deflector for deflecting an electron beam to the specimen to form images;
an image pickup device for obtaining the images; and
a processor coupled to the image pickup device being programmed for observing the specimen in a field of view of the electron microscope, said programming comprising the act of:
calculating a phase only correlation or a phase-amplitude correlation of images obtained by differential electro-optical conditions of the electron microscope;
determining whether the image of the field of view is suitable or not for an observation based on calculated degree; and
moving the field of view to a next position when the image of the field of view is determined to be not suitable.

3. A method of observing a specimen in a field of view of an electron microscope comprising the acts of:
deflecting an electron beam to the specimen to form images;
acquiring said images from the specimen using an image pickup device; and
observing the images in a field of view of the electron microscope using programming from a processor, said programming including the acts of:
calculating a degree of coincidence of images obtained by differential electro-optical conditions of the electron microscope;
determining whether the image of the field of view is suitable or not for an observation based on calculated degree; and
moving the field of view to a next position when the image of the field of view is determined to be not suitable.

* * * * *